United States Patent
Hortobágyi et al.

(10) Patent No.: US 11,319,274 B2
(45) Date of Patent: May 3, 2022

(54) PROCESS FOR THE PREPARATION OF POLYMORPH FORM B OF TREPROSTINIL DIETHANOLAMINE SALT

(71) Applicant: CHINOIN GYÓGYSZER ÉS VEGYÉSZETI TERMÉKEK GYÁRA ZRT., Budapest (HU)

(72) Inventors: Irén Hortobágyi, Budapest (HU); István Lászlófi, Budapest (HU); Zoltán Varga, Budapest (HU); Imre Juhász, Budapest (HU); Imola Ritz, Budapest (HU); Zsuzsanna Kardos, Budapest (HU)

(73) Assignee: CHINOIN GYÓGYSZER ÉS VEGYÉSZETI TERMÉKEK GYÁRA ZRT., Budapest (HU)

(*) Notice: Subject to any disclaimer, the term of this patent is extended or adjusted under 35 U.S.C. 154(b) by 0 days.

(21) Appl. No.: 16/978,391

(22) PCT Filed: Mar. 7, 2019

(86) PCT No.: PCT/HU2019/050007
§ 371 (c)(1),
(2) Date: Sep. 4, 2020

(87) PCT Pub. No.: WO2019/171093
PCT Pub. Date: Sep. 12, 2019

(65) Prior Publication Data
US 2021/0053901 A1    Feb. 25, 2021

(30) Foreign Application Priority Data
Mar. 9, 2018 (HU) .................................. P1800089

(51) Int. Cl.
*C07C 51/43* (2006.01)
*C07C 59/72* (2006.01)
*C07C 215/10* (2006.01)

(52) U.S. Cl.
CPC .......... *C07C 51/43* (2013.01); *C07B 2200/13* (2013.01); *C07C 59/72* (2013.01); *C07C 215/10* (2013.01)

(58) Field of Classification Search
None
See application file for complete search history.

(56) References Cited

U.S. PATENT DOCUMENTS
2016/0152548 A1   6/2016  Gao et al.

FOREIGN PATENT DOCUMENTS
| IN | 02963CH2014 | 6/2014 |
| WO | WO 2005/007081 A2 | 1/2005 |
| WO | WO 2009/078965 A1 | 6/2009 |

OTHER PUBLICATIONS

Batra et al., "Crystallization Process Development for a Stable Polymorph of Treprostinil Diethanolamine (UT-15C) by Seeding", Organic Process Research and Development, 2009, vol. 13. pp. 242-249.

(Continued)

*Primary Examiner* — Sudhakar Katakam
*Assistant Examiner* — Jennifer C Sawyer
(74) *Attorney, Agent, or Firm* — Birch, Stewart, Kolasch & Birch, LLP

(57) ABSTRACT

The invention relates to a robust and reproducible process for the preparation of polymorph form B of treprostinil diethanolamine salt, comprising the following steps: a. treprostinil is dissolved in methanol, b. to the solution of step a) diethanolamine or its methanol solution is added, c. the reaction mixture of step b) is agitated till dissolution, d.

(Continued)

Figure 1:
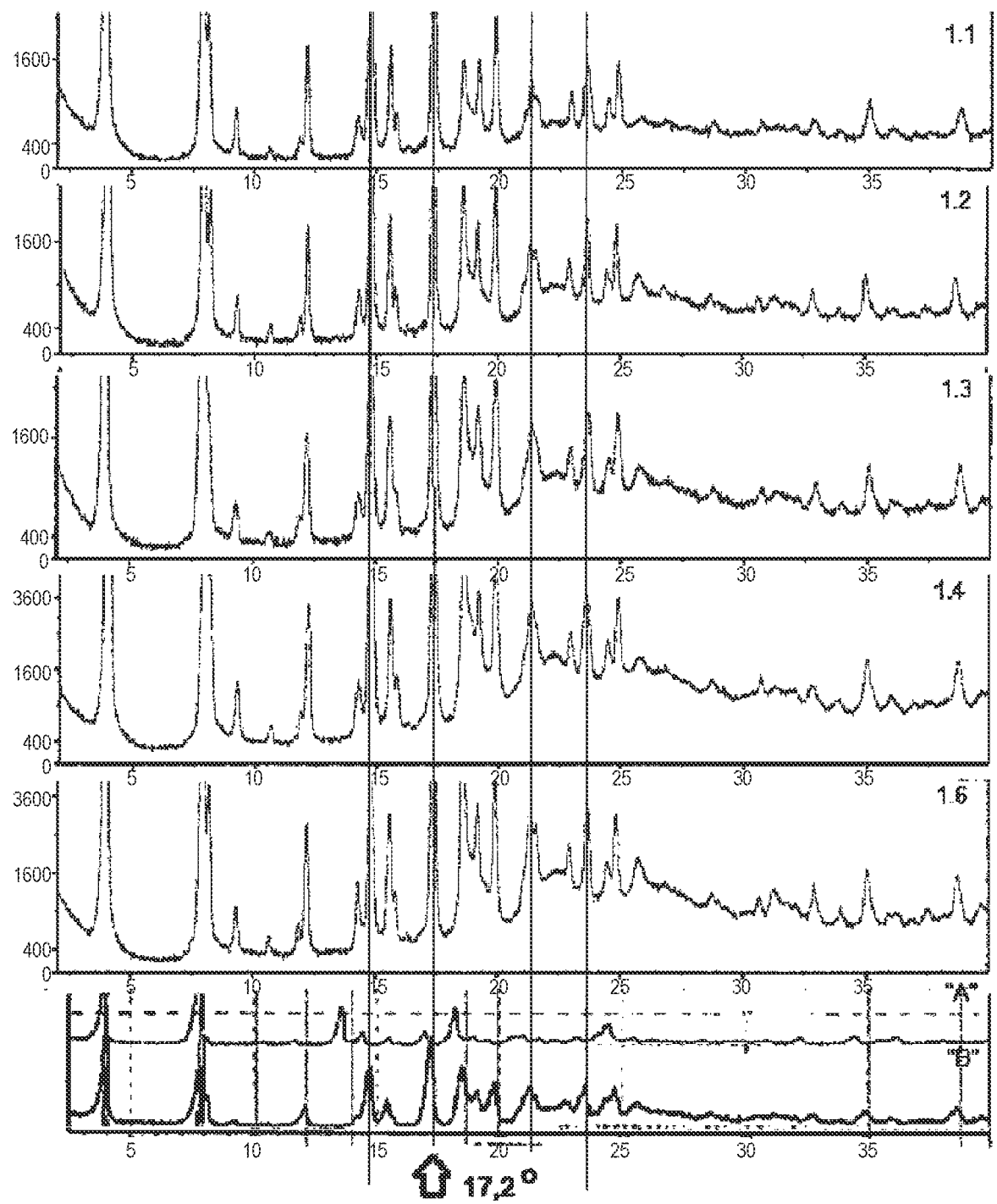

when salt formation is completed in step c), first portion of an aprotic solvent is added to the solution, e. the solution of step d) is filtered to remove insoluble impurities, f. the filtrate of step e) is seeded with polymorph form B of treprostinil diethanolamine salt, g. to the crystal suspension obtained in step f) a second portion of the aprotic solvent is added, h. the suspension of step g) is agitated until crystallisation is completed, i. the crystals are separated, washed and dried.

15 Claims, 21 Drawing Sheets

(56) References Cited

OTHER PUBLICATIONS

International Search Report, issued in PCT/HU2019/050007, dated Oct. 4, 2019.
Written Opinion of the International Searching Authority, issued in PCT/HU2019/050007, dated Oct. 4, 2019.

Fig. 21

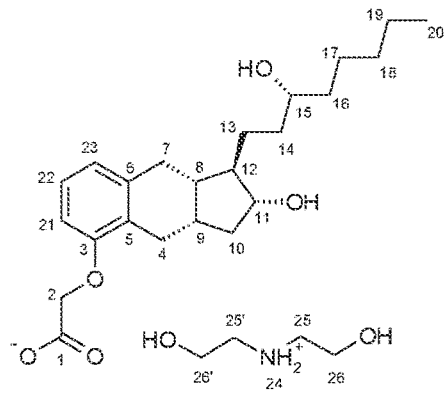

| Numbering | ¹³C (ppm) | ¹H (ppm) | Number of ¹H | Multiplicity | Coupling constant (Hz) (+/- 0.2Hz) |
|---|---|---|---|---|---|
| 1 | 172.27 | - | - | - | |
| 2 | 67.18 | 4.27 | 2 | s | |
| 3 | 155.48 | - | - | - | |
| 4 | 25.72 | 4β: 2.735<br>4α: 2.40* | 1<br>1 | dd<br>m (dd) | $J_{4gem}$=14.6; $J_{4\beta,9}$=6.2<br>$J_{4\alpha,9}$=6.8 |
| 5 | 126.43 | - | - | - | |
| 6 | 140.12 | - | - | - | |
| 7 | 33.49 | 7β: 2.66<br>7α: 2.37* | 1<br>1 | dd<br>m (dd) | $J_{7gem}$=14.2; $J_{7\beta,8}$=6.2<br>$J_{7\alpha,8}$=6.7 |
| 8 | 40.57 | 1.74 | 1 | m (dddd/tt) | $J_{8,9}$=10.0; $J_{8,12}$=9.0 |
| 9 | 32.50 | 2.09 | 1 | m (ddddd) | |
| 10 | 41.21 | 10β: 1.96<br>10α: 1.01 | 1<br>1 | m (ddd/dt)<br>m (ddd/dt) | $J_{10gem}$=11.8; $J_{9,10\beta}$~7.0;<br>$J_{10\beta,11}$~6.2<br>$J_{9,10\alpha}$~$J_{10\alpha,11}$~10.2 |
| 11 | 75.51 | 3.47 | 1 | m (td) | $J_{11,12}$~9.5 |
| 12 | 51.54 | 1.10 | 1 | tt | $J_{12,13}$=6.1 |
| 13 | 28.37 | 13a: 1.605<br>13b: 1.31** | 1<br>1 | m (dq)<br>m | |
| 14 | 35.04 | 14a: 1.445<br>14b: 1.42 | 1<br>1 | m<br>m | |
| 15 | 70.13 | 3.35 | 1 | m (tt) | 7.1, 4.1 |
| 16 | 37.04 | 16a: 1.34<br>16b: 1.28 | 1<br>1 | m<br>m | |
| 17 | 24.94 | 17a: 1.37<br>17b: 1.25 | 1<br>1 | m<br>m | |
| 18 | 31.52 | 18a: 1.26<br>18b: 1.19 | 1<br>1 | m<br>m | |
| 19 | 22.16 | 1.27** | 2 | m | |
| 20 | 13.95 | 0.865 | 3 | t | $J_{19,20}$=7.0 |
| 21 | 109.42 | 6.61 | 1 | d | $J_{21,22}$=8.2 |
| 22 | 125.64 | 6.98 | 1 | t | $J_{22,23}$=7.4 |
| 23 | 119.69 | 6.68 | 1 | d | |
| 25, 25' | 49.66 | 2.885 | 4 | t | $J_{25,26}$=5.4 |
| 26, 26' | 57.29 | 3.595 | 4 | t | |

PROCESS FOR THE PREPARATION OF POLYMORPH FORM B OF TREPROSTINIL DIETHANOLAMINE SALT

TREPROSTINIL OF FORMULA (II)

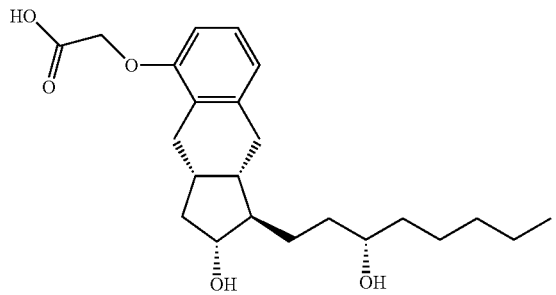

is a synthetic prostacyclin derivative with platelet aggregation inhibitory and vasodilatory effects. It is the only prostacyclin derivative which may be applied subcutan, intravenously, or in inhalatory and oral forms.

Its therapeutic fields involve the treatment of pulmonary arterial hypertension (Pulmonary Arterial Hypertension, PAH), *Drugs,* 2012, 72 (18) 2351-2363) and chronic thromboembolic pulmonary hypertension. http://www.europa.eu/docs/en GB/document library/Orphan designation/ 2009/10/WC500005505.pdf, download: 15 Feb. 2017.)

Treprostinil sodium salt of formula (III)

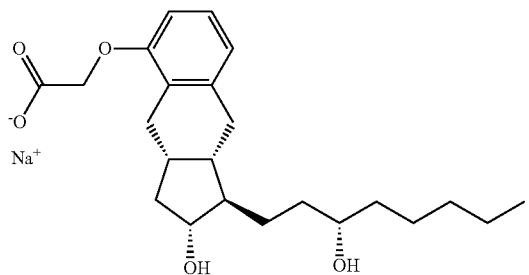

is on the market for injection use under the name Remodulin, for inhalatory purpose under the name Tyvaso®.

Treprostinil diethanolamine salt of formula (I) is the active ingredient of Orenitram®, formulated as tablets.

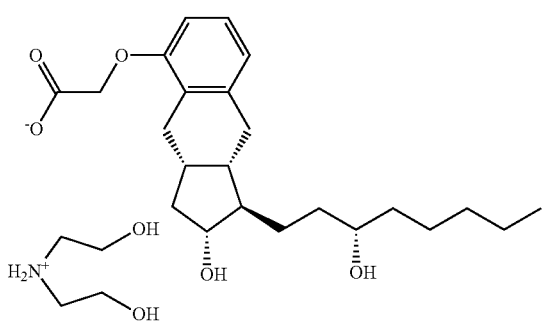

The two polymorph forms (forms A and B) of the crystalline treprostinil diethanolamine salt were first described in patent specification WO2005/007081. The polymorph forms were characterized by their melting point, X-ray powder diffraction pattern, DSC (Differential Scanning calorimetry) and TGA (Thermogravimetric Analysis) curves, and by their hygroscopic character.

They stated that
- the metastable form A is hygroscopic, it melts at 103° C., the DSC curve exhibits endothermic peak at 103° C., and as shown by TGA, the crystals do not contain any solvated solvent
- the more stable form B is much less hygroscopic, it melts at 107° C., the DSC curve exhibits endothermic peak at 107° C., the TGA curve shows a minimal weight loss at 100° C.
- forms A and B exhibit different powder diffractograms: the characteristic peak of the more stable crystalline form B is 17.2° Theta.
- form A in suspension made with various organic solvents (1,4-dioxane, isopropanol, tetrahydrofuran, toluene) transforms into form B on agitation at different temperatures.

Publication Organic Process & Development, 2009, 13, 242-249. (Crystallization Process Development for Stable Polymorph of Treprostinil; Batra, H.; Penmasta, R.; Phares, K.; Staszewski, J.; Tuladhar, S. M; D. A. Walsh, United Therapeutics) describes in detail the physical characteristics of the two polymorphs and the experiments carried out for their preparation. The metastable form A, which was isolated first, on standing transforms into the thermodynamically more stable form B.

Several solvent-antisolvent mixtures of various ratio were investigated. From isopropanol:methyl tert-butyl ether (TBME) mixtures mainly form A was obtained, but agitating the crystal suspension for several hours, form A transformed into form B, this transformation, however, did not take place when scaled-up.

Crystallisation from ethanol:acetone=7:1 (yield 85-90%) and from ethanol:ethyl acetate=7:1 (yield>90%) mixtures lead to form B, uniformly, if the solution was seeded with form B, and cooling was very slow, controlled with several temperature steps.

Patent specification WO 2009/078965 discloses the preparation of high purity treprostinil Na salt through crystalline treprostinil diethanolamine salt.

To the solution of treprostinil in ethyl acetate, anhydrous ethanol and diethanolamine were added. The clear solution was agitated at 60-75° C. for 30-60 minutes, cooled to 55±5° C. and seeded with 1% amount of polymorph form B of treprostinil diethanolamine salt. The precipitated crystals were agitated for 1 hour while keeping the temperature, then the crystal suspension was cooled to 20-22° C. After 16-24 hours of agitation the crystals were collected by filtration, washed with ethyl acetate and dried, yield 88%.

If the melting point of the treprostinil diethanolamine crystals was >104° C., then form B was obtained.

If the melting point of the resulting treprostinil diethanolamine crystals was <104° C., then the mixture of forms A and B was present. In that case the crystal mixture was repeatedly crystallized with ethanol:ethyl acetate solvent mixture.

The above described process is thus neither robust, nor reproducible, often the mixture of forms A+B is obtained.

Patent specification WO 2014/089385 describes the preparation of treprostinil, treprostinil Na and treprostinil diethanolamine salts.

For the preparation of treprostinil diethanolamine salt, the ethyl acetate solution of treprostinil was treated with the solution of diethanolamine in anhydrous ethanol, the obtained suspension was heated and kept at reflux temperature for 15 minutes while all components dissolved. The solution was then slowly, during 18 hours, cooled to room temperature. The precipitated white crystalline material was filtered off, washed with ethyl acetate and dried in vacuum at 50° C. for 24 hours. Yield 76%. Physical characteristics of the salt are not given.

Patent specification IN 2014CH02963-A discloses the preparation of treprostinil, treprostinil Na and treprostinil diethanolamine salts.

To the aqueous solution of diethanolamine the acetone solution of treprostinil was added at 25-30° C. Optionally, the solution was seeded, then agitated for 15 minutes while keeping the temperature. The crystal suspension was cooled to 0-5° C., after 90 minutes of agitation the crystals were filtered off, washed and dried. Yield: 79%, polymorph A.

The polymorph A crystals of treprostinil diethanolamine salt were suspended in acetone, then at reflux temperature approx. 0.2% amount of ethanol was added to the suspension. After 6 hours of agitation at reflux temperature followed by cooling to 25-30° C. the crystals were filtered off, washed and dried. Yield 100%, polymorph B.

In the above described process, polymorph B of treprostinil diethanolamine salt could only be prepared in two steps.

In the process described in patent specification US 2016/0152548, to form the salt treprostinil and diethanolamine were dissolved in ethanol and ethyl acetate at 70° C., after 30 minutes of agitation the solution was cooled to 55° C., seeded with 1% by weight of seeding crystals of treprostinil diethanolamine salt polymorph B, the suspension was agitated at 55° C. for 1 hour and cooled to room temperature. After 16 hours of agitation the crystals were filtered off, washed and dried. Yield: 93%. Physical characteristics of the crystals (melting point, X-ray powder diagram, DSC, TGA) are not given.

In the above described process again, ethanol-ethyl acetate mixture was used for the crystallisation, similarly to the process of patent specification WO 2014/089385, which is known not to be robust and reproducible, and results, in many cases, the mixture of forms A+B.

Our aim was to develop a process for the preparation of crystalline treprostinil diethanolamine salt, which is robust, well reproducible, and provides the more stable polymorph form B of the salt in one step (i.e. one crystallization step of treprostinil diethanolamine salt comprising the sequence of seeding, antisolvent addition, cooling and filtering).

It is known from the literature that treprostinil diethanolamine salt may crystallize in two polymorph forms. Polymorph form with the lower melting point (melting point 103° C.) is the metastable form A, while the one with higher melting point (melting point 107° C.) is the thermodynamically more stable form B, therefore, to prepare the pharmaceutical active ingredient, polymorph B is the desired form.

Preparation of the thermodynamically more stable form B is, however, not an easy task:

even if we find an appropriate solvent-antisolvent ratio, carry out the dissolution at reflux temperature, apply seeding with form B, perform the cooling very slowly in a controlled way with several temperature steps, it is not assured that the process will provide the more stable form B in every case. As shown by the literature, often may occur that even if the pre-determined parameters are strictly followed, forms A and B crystallize together, and the desired polymorph is finally obtained from a mixture of crystal forms A and B after an additional operational step (repeated crystallisation, long agitation of the crystal suspension).

We organized the data of the literature and investigated which of the crystal forms is obtained by using various solvents or solvent mixtures. (Table I.)

TABLE I

Methods from the literature to prepare crystalline Treprostinil DEA

| | Reference | Method | Solvent/antisolvent | Form | Yield [%] | Comments |
|---|---|---|---|---|---|---|
| 1 | WO2005/007081 | 1* | tetrahydrofuran | A | no data | |
| | | | water | A + B | no data | |
| | | | EtOH:water | A + B | no data | |
| | | 2** | dioxane | B | no data | |
| | | | toluene | A + B | no data | |
| | | | isopropanol | B | no data | |
| | | | tetrahydrofuran | B + A | no data | |
| 2 | Org. Proc. Res. & Dev. 2009. | 2** | isopropanol | A + B | no data | at scale-up |
| | | | isopropanol:TBME | A + B | no data | form A does not transform into form B |
| | | 1* | isopropanol:TBME | A | no data | |
| | | 1* | EtOH:acetone = 1:5 | A + B | no data | the process is not robust |
| | | | EtOH:acetone = 1:6 | A + B | no data | |
| | | | EtOH:acetone = 1:7 | B*** | no data | |
| | | | EtOH:acetone = 1:8 | A + B | no data | |
| | | | EtOH:acetone = 1:10 | B*** | 94**** | |
| | | 1* | EtOH:EtOAc = 1:5 | A + B | no data | the process is not robust |
| | | | EtOH:EtOAc = 1:6 | A + B | no data | |
| | | | EtOH:EtOAc = 1:7 | B*** | no data | |
| | | | EtOH:EtOAc = 1:8 | B*** | 95**** | |
| | | | EtOH:EtOAc = 1:10 | A + B | no data | |
| 3 | WO2009/078965 | 1* | EtOH:EtOAc = 1:7 | B*** | 88 | if A + B precipitates, repeated crystallisation is needed |
| 4 | WO2014/089385 | 1* | EtOH:EtOAc = 1:8 | | 76 | the crystal form is not characterized, but the method is not robust |

TABLE I-continued

Methods from the literature to prepare crystalline Treprostinil DEA

| Reference | Method | Solvent/antisolvent | Form | Yield [%] | Comments |
|---|---|---|---|---|---|
| 5 IN 2014CH02963A | 1*<br>2** | water:acetone = 1:90<br>acetone:EtOH = 600:1 | A<br>B | 79 | form A<br>form A is transformed into form B |
| 6 US2016/0152548 | 1* | EtOH:EtOAc = 1:7 | | 93 | the crystal form is not characterized, but the method is not robust |

*crystallisation from solution
**agitation of the crystal suspension containing form A or forms A + B
***scaled-up crystallisation
****if A + B precipitates, crystallisation is repeated From Table I., which is simplified and does not contain the temperature profile of the crystallisations, the following conclusions may be drawn:

Crystallisation processes of patent specification WO 2005/007081 (1) lead to form A, or to the mixture of forms A+B. The desired form B could be obtained by subsequent agitation of the crystal suspension for several days.

According to the publication (2) of Org. Proc. Res.&Dev.:
During the laboratory experiments the primarily obtained form A and also the mixture of forms A+B fully transformed into form B on the effect of long agitation with isopropanol or with isopropanol:methyl tert.-butyl ether mixtures, however, during scale-up it did not succeed to obtain form B.

Crystallisation from isopropanol:methyl tert.-butyl ether mixtures provided form A.

By crystallisation from EtOH:acetone mixtures, the 1:7 ratio mixture lead generally to form B, but sometimes the mixture of forms A+B was obtained. In that case, the crystallisation had to be repeated until uniformly form B crystals were obtained. During the process the solution had to be seeded with crystalline form B, a complicated temperature profile had to be followed and the whole crystallisation took 3 days. The process is, however, not robust, as only a small change in the solvent ratio could cause that the mixture of forms A+B is crystallized. It is surprising, that instead of solvent mixture EtOH:acetone=1:7 determined in the laboratory experiments, EtOH:acetone=1:10 mixture was chosen during scale-up.

By crystallisation from EtOH:ethyl acetate mixtures, the 1:7 ratio mixture lead generally to form B, but in some cases the mixture of forms A+B was obtained. In that cases crystallisation had to be repeated until uniformly form B crystals were obtained. During the process, the solution had to be seeded with crystalline form B, and a complicated temperature profile had to be followed, the whole crystallisation needed shorter time, approx. 1.5 days. The process is, however, not robust with this solvent mixture either, since a small change in the solvent ratio could lead to the crystallisation of a mixture of forms A+B. It is surprising, that in this method, too, for scale-up another solvent ratio (EtOH:ethyl acetate=1:8) was chosen, and not the one (EtOH:ethyl acetate=1:7) found most suitable during the laboratory experiments In patent specification WO 2009/078965 A1 (3) crystallisation of treprostinil diethanolamine salt was carried out with EtOH:ethyl acetate=1:7 mixture. If not form B crystallized, the crystallisation had to be repeated, the process is thus not robust.

In patent specification WO 2014/089385 A2 (4) crystallisation of treprostinil diethanolamine salt was carried out with EtOH:ethyl acetate=1:8 mixture. The crystal form was not characterized, but it is known from literature data that this method is not robust for the preparation of form B.

According to patent specification IN 2014CH02963 (5) treprostinil diethanolamine salt was crystallized from acetone:water mixture which provides form A. Crystal form A, on agitation in acetone:EtOH mixture transformed into form B.

In the process of patent specification US 2016/0152548 A1 (6) treprostinil diethanolamine salt was crystallized with EtOH:ethyl acetate=1:7 solvent mixture. According to the description form B was obtained, but it is known from literature data that this method is not robust.

For industrial implementation, however, it is essential for a technology to be robust, simple, scalable, reproducible and easy to carry out.

In the light of the above, we aimed to develop a process providing treprostinil diethanolamine salt of formula I in the form of the thermodynamically more stable crystalline polymorph B reproducibly, in every case, in one step.

We carried out numerous experiments to develop the method for preparing polymorph form B of treprostinil diethanolamine salt. Our aim was to perform the salt formation using such a solvent from which solely polymorph B crystallizes.

In the experiments 1.0 g of treprostinil (II) was dissolved in the selected solvents. To the solution 0.3 g of diethanolamine (IV) was added and the reaction mixture was agitated at 35° C. for 30 minutes. To the homogenous solution the first portion of the antisolvent was added, the mixture was then cooled to room temperature and seeded with polymorph B of treprostinil diethanolamine salt (I). After 1-2 hours of agitation the second portion of the antisolvent was added to the crystal suspension and agitation at room temperature was continued for additional 16-24 hours.

Treprostinil diethanolamine (I) crystals were filtered off, washed and dried in vacuum at 45° C. The crystal form was determined by DSC and X-ray powder diffraction (XRPD) investigation.

To our surprise we found that from methanol with any of the antisolvents (methyl tertiary-butyl ether, acetone, ethyl acetate, diisopropyl ether, acetonitrile) only form B was crystallized, (for X-ray powder diffractograms see FIG. 1.), whereas using the solvents described in the literature both forms A and B were formed.

TABLE II

Preparation of crystalline treprostinil diethanolamine salt from methanol

| No. of the Example in the application | Methanol (ml) | Antisolvent Name | Portion 1. (ml) | Portion 2. (ml) | Yield (%) | Crystal form (DSC, XRPD) |
|---|---|---|---|---|---|---|
| 1. | 4 | methyl tertiary-butyl ether | 15 | 20 | 91 | B |
| 2. | 4 | acetone | 15 | 20 + 10 | 73 | B |
| 3. | 4 | ethyl acetate | 15 | 20 | 92 | B |
| 4. | 6 | diisopropyl ether | 10 | 20 | 95 | B |
| 5. | 6 | toluene | 10 | 20 + 10 | did not crystallize | — |
| 6. | 4 | acetonitrile | 15 | 20 | 91 | B |

It is to be noted that toluene is not a suitable antisolvent to crystallize treprostinil diethanolamine salt, it was not successful to obtain the salt in crystalline form using toluene.

The most suitable solvent to prepare the crystalline polymorph form B of treprostinil diethanolamine salt was found to be methanol, since carrying out the crystallisation from this solvent, always uniformly form B crystallizes.

As antisolvent methyl tertiary-butyl ether was chosen, because of technological reasons this solvent proved to be most suitable.

Formation of treprostinil diethanolamine salt was repeated four-times in 1 g sizes by using methanol-methyl tertiary-butyl ether as solvent-antisolvent mixture, then the process was scaled-up, starting from 70 g of treprostinil (II) (example 7). In every case, uniformly polymorph form B of the salt was obtained.

Our process is thus robust, reproducible, and gives the desired form B in one step.

In addition, our process is technically more convenient because there is no need for programmed cooling, that is used in the prior art process.

To justify further the robustness of our process, preparation of treprostinil diethanolamine salt was repeated five times in 1 g size. The quantity of methyl tertiary-butyl ether, the antisolvent for crystallization was varied in a wide range.

Treprostinil (II) was dissolved in methanol (4 ml), diethanolamine (0.3 g) was added to the solution. After completion of salt formation, the first portion of methyl tertiary-butyl ether was added (15 ml).

The solution was filtered and the second portion of methyl tertiary-butyl ether was added dropwise to complete the crystallization.

In all cases form B of treprostinil diethanolamine was crystallized as evidenced by XRPD and DSC. The characteristic peak of form B, i.e. 17.2° 2Theta is present in the XRPD pattern while characteristic peaks of form A are completely missing. Further, DSC exhibits endothermic peak at a temperature which is equal to or higher than around 105° C. in all cases.

| Example | Quantity of TBME | Ratio of Me:OH:TBME | Yield |
|---|---|---|---|
| 8 | 15 ml + 20 ml | 1:8.75* | 91% |
| 9 | 15 ml + 25 ml | 1:10 | 91% |

-continued

| Example | Quantity of TBME | Ratio of Me:OH:TBME | Yield |
|---|---|---|---|
| 10 | 15 ml + 29 ml | 1:11 | 92% |
| 11 | 15 ml + 9 ml | 1:6 | 81% |
| 12 | 15 ml + 5 ml | 1:5 | 75% |

*ratio used for scale-up

Crystallisation was also carried out using ethanol-ethyl acetate solvent-antisolvent mixture. In this case, in agreement with the literature data, the mixture of forms A+B was obtained (example 13.). If this mixture of forms A and B of treprostinil diethanolamine salt was crystallized from methanol-methyl tertiary-butyl ether solvent mixture, uniformly polymorph form B of the salt was obtained (example 14.).

Dissolving treprostinil diethanolamine salt in aqueous methanol (approx. 30% of water) and carrying out the precipitation with acetone, we obtained again polymorph form B uniformly, but the yield was only 61% (example 15.).

Polymorph form B of treprostinil diethanolamine salt was obtained also if the salt was dissolved in methanol, the solution was set to opalescent with methyl tertiary-butyl ether at 45° C. and then crystallisation was completed at room temperature (yield 87%) (example 16.). However, crystallisation from the methanol-methyl tertiary-butyl ether solvent mixture at −70° C., afforded low melting point, highly hygroscopic crystals. This form is named polymorph form C (example 17.). Polymorph form C is a less stable form with melting point 86-88° C., on the basis of the DSC curve, and in the DSC tube it transforms into the more stable, higher melting point (101-103° C.) form.

Based on the above, the subject of our invention is process for the preparation of polymorph form B of treprostinil diethanolamine salt, comprising the following steps:
  a. treprostinil is dissolved in methanol,
  b. to the solution of step a) diethanolamine or its methanol solution is added,
  c. the reaction mixture of step b) is agitated till dissolution,
  d. when salt formation is completed in step c), first portion of an aprotic solvent is added to the solution, e. the solution of step d) is filtered to remove insoluble impurities,
f. the filtrate of step e) is seeded with polymorph form B of treprostinil diethanolamine salt,
g. to the crystal suspension obtained in step f) a second portion of the aprotic solvent is added,
h. the suspension of step g) is agitated until crystallisation is completed,
i. the crystals are separated, washed and dried.

A further subject of our invention is a process for the transformation of polymorph form A or of the mixture of polymorph forms A and B of treprostinil diethanolamine salt into polymorph form B, uniformly, comprising the following steps:
a. treprostinil diethanolamine salt is dissolved in methanol,
b. to the solution of step a) a first portion of aprotic solvent is added,
c. the solution of step b) is filtered to remove insoluble impurities,
d. the filtrate of step c) is seeded with polymorph form B of treprostinil diethanolamine salt,
e. to the crystal suspension of step d), a second portion of the aprotic solvent is added,
f. the suspension of step e) is agitated until crystallisation is completed,
g. the crystals are separated, washed and dried.

In a preferred embodiment of the invention, dissolution of treprostinil and diethanolamine or of treprostinil diethanolamine salt is performed at 25-50° C., favourably at 30-40° C.

As for aprotic solvent ethers, such as methyl tertiary-butyl ether, diisopropyl ether, ketone-type solvent, such as acetone, ester-type solvent, such as ethyl acetate or acetonitrile, preferably methyl tertiary-butyl ether are applied.

The solvent (methanol):antisolvent ratio is preferably 1:4-20, more preferably 1:5-15, and even more preferably 1:7-11.

In an embodiment of the process according to the invention crystalline form B of treprostinil diethanolamine salt is prepared in a way that treprostinil is dissolved in methanol at 35° C., solid diethanolamine base is added to it and the mixture is agitated at 35° C. till dissolution. The first portion of the antisolvent methyl tertiary-butyl ether, is then added to it, the solution is filtered, the filtrate solution is seeded with polymorph form B of treprostinil diethanolamine salt and the mixture is agitated at room temperature. To the crystal suspension the second portion of the antisolvent is added and the mixture is agitated at room temperature, until crystallisation is completed. Recrystallisation of polymorph form A or the mixture of polymorph forms A and B of treprostinil diethanolamine salt from methanol-methyl tertiary-butyl ether affords form B of treprostinil diethanolamine salt.

Advantages of our process, compared to previous methods:
the method is simple, robust, scalable and well reproducible,
it provides the desired form B in one step,
application is easy to scale-up because of the complicated heating-cooling profiles is not needed,
the followings are not required: subsequent transformation of the crystal form,
repeated crystallisation and/or
long agitation of the crystal suspension, and/or
complicated heating-cooling profiles
it provides reproducibly the desired, more stable polymorph form B,
the method is equally suitable to obtain form B of treprostinil diethanolamine salt
via salt formation starting from treprostinil and diethanolamine (IV), followed by crystallisation of the resulting salt,
via transformation of form A or the mixture of forms A+B into uniformly form B, by crystallisation.

Details of our invention are demonstrated by the following examples, without limiting the invention thereto.

Conditions of the measurements applied in the processes according to the invention:
X-ray Diffractograms:
Starting position [°2Theta]: 2.0084
End position [°2Theta]: 39.9864
Temperature of measurement [° C.]: 25.00
Material of the anode: Cu
K-Alpha1 [Ĺ]: 1.54060
K-Alpha2 [Ĺ]: 1.54443
DSC:
Instrument: METTLER TOLEDO DSC1 STARe System, Stare basic V9.30
Method: Starting temperature: 30° C.
Final temperature: 150° C.
Heating rate: 5° C./min
Amount: 2-6 mg, perforated aluminum crucible (40 μl)
NMR:
Instrument: Bruker Avance III 500 MHz
Solvent: DMSO

BRIEF DESCRIPTION OF DRAWINGS/FIGURES

FIG. 1: X-Ray powder diffraction patterns of different polymorph forms of treprostinil diethanolamine salt crystallized from methanol as solvent and different-antisolvents (examples 1 to 6):
1.1: MeOH/methyl tertiary-butyl ether
1.2: MeOH/acetone
1.3: MeOH/ethyl-acetate
1.4: MeOH/diisopropyl ether
1.6: MeOH/acetonitrile
"A": Treprostinil diethanolamine polymorph form A
"B": Treprostinil diethanolamine polymorph form B
FIG. 2: XRPD pattern of treprostinil diethanolamine salt polymorph form B crystallized from MeOH/methyl tertiary-butyl ether mixture (example 7)
FIG. 3: DSC curve of treprostinil diethanolamine salt polymorph form B crystallized from MeOH/methyl tertiary-butyl ether mixture (peak: 106.56° C., example 7)
FIG. 4: XRPD pattern of treprostinil diethanolamine salt polymorph form B crystallized from MeOH/methyl tertiary-butyl ether mixture (example 8)
FIG. 5: DSC curve of treprostinil diethanolamine salt polymorph form B crystallized from MeOH/methyl tertiary-butyl ether mixture (peak: 106.23° C., example 8)
FIG. 6: XRPD pattern of treprostinil diethanolamine salt polymorph form B crystallized from MeOH/methyl tertiary-butyl ether mixture (example 9)
FIG. 7: DSC curve of treprostinil diethanolamine salt polymorph form B crystallized from MeOH/methyl tertiary-butyl ether mixture (peak: 105.37° C., example 9)
FIG. 8: XRPD pattern of treprostinil diethanolamine salt polymorph form B crystallized from MeOH/methyl tertiary-butyl ether mixture (example 10)

Figure 9:
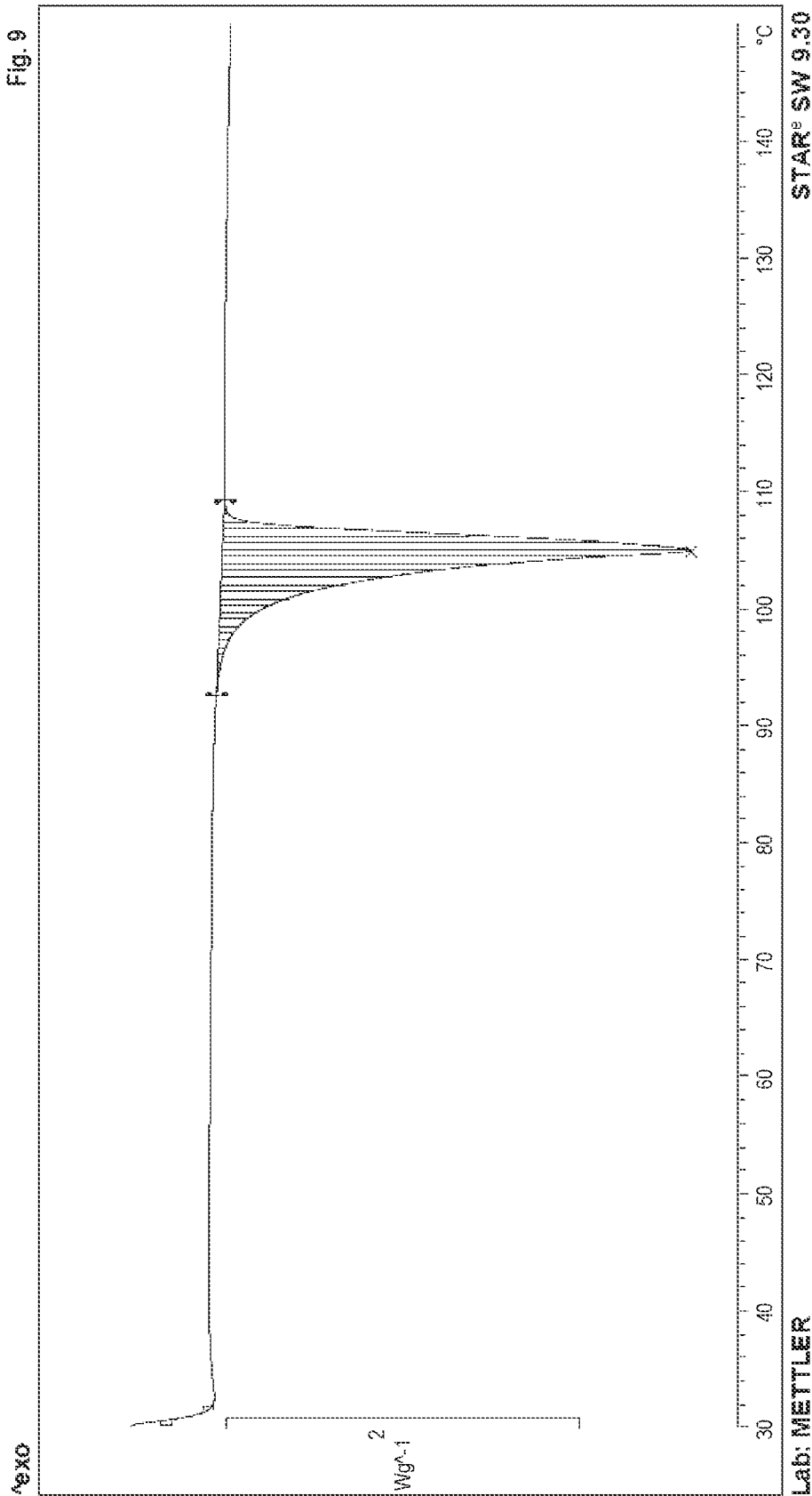

FIG. 9: DSC curve of treprostinil diethanolamine salt polymorph form B crystallized from MeOH/methyl tertiary-butyl ether mixture (peak: 104.91° C., example 10)

Figure 10:
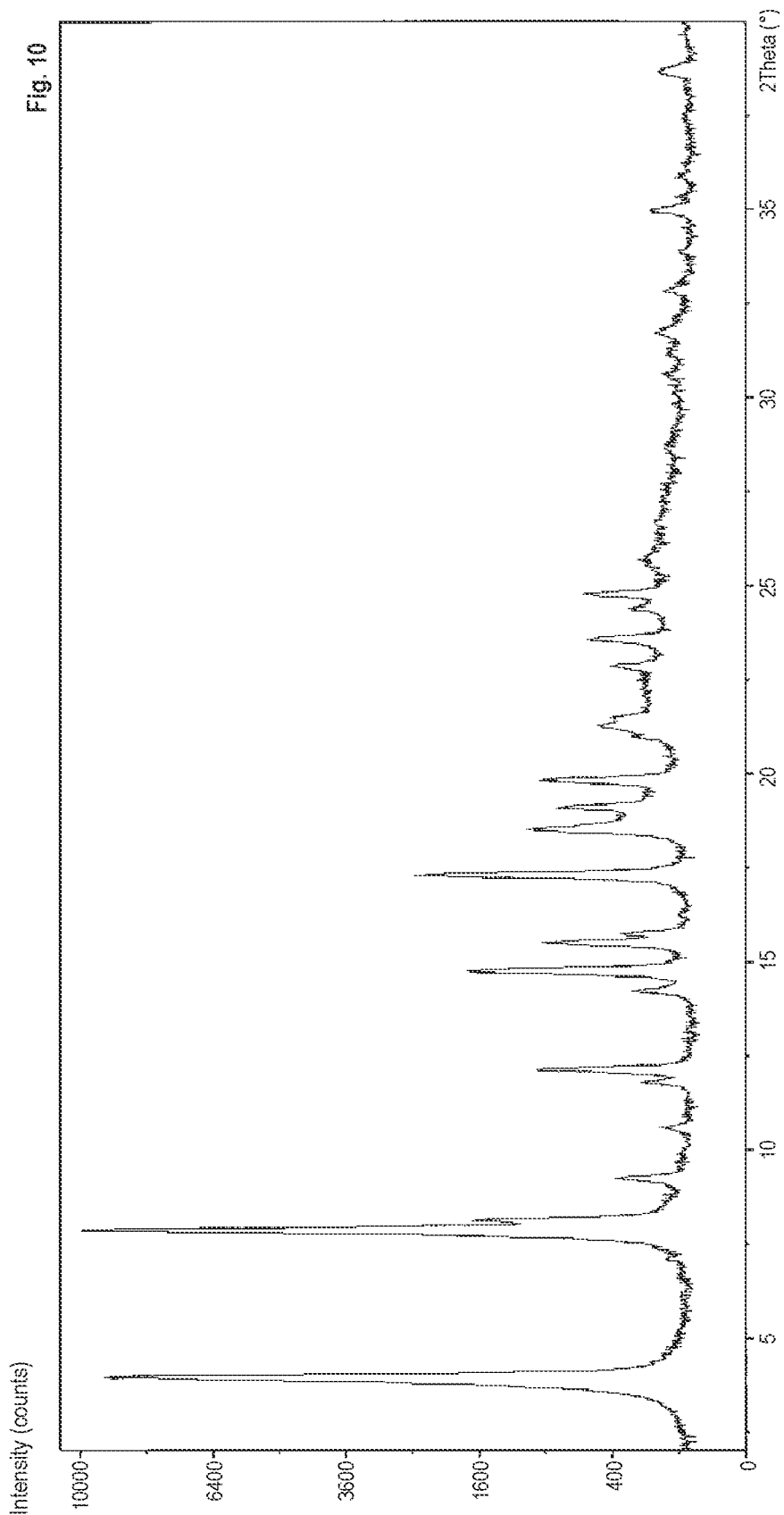

FIG. 10: XRPD pattern of treprostinil diethanolamine salt polymorph form B crystallized from MeOH/methyl tertiary-butyl ether mixture (example 11)

Figure 11:
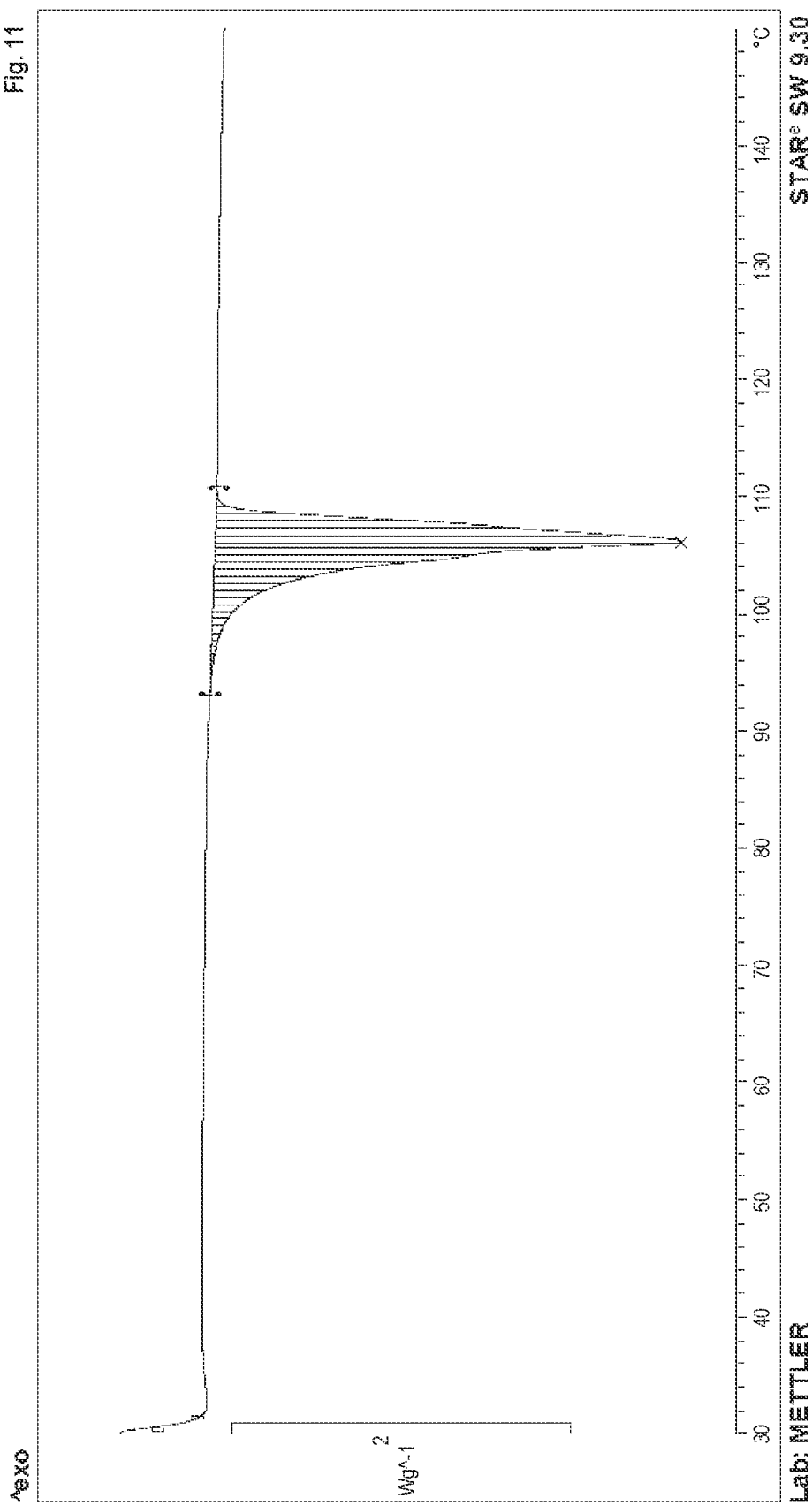

FIG. 11: DSC curve of treprostinil diethanolamine salt polymorph form B crystallized from MeOH/methyl tertiary-butyl ether mixture (peak: 106.10° C., example 11)

Figure 12:
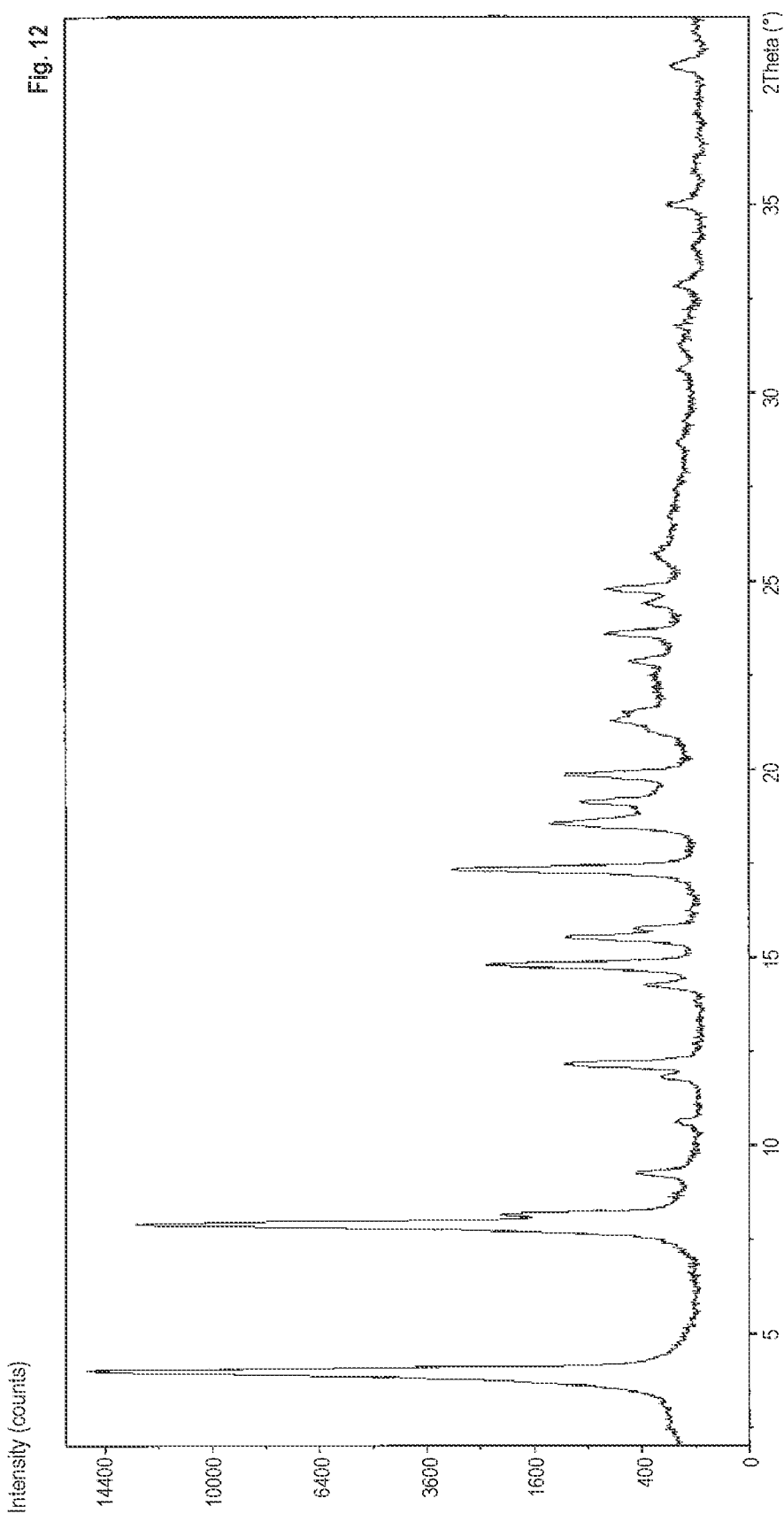

FIG. 12: XRPD pattern of treprostinil diethanolamine salt polymorph form B crystallized from MeOH/methyl tertiary-butyl ether mixture (Example 12)

Figure 13:
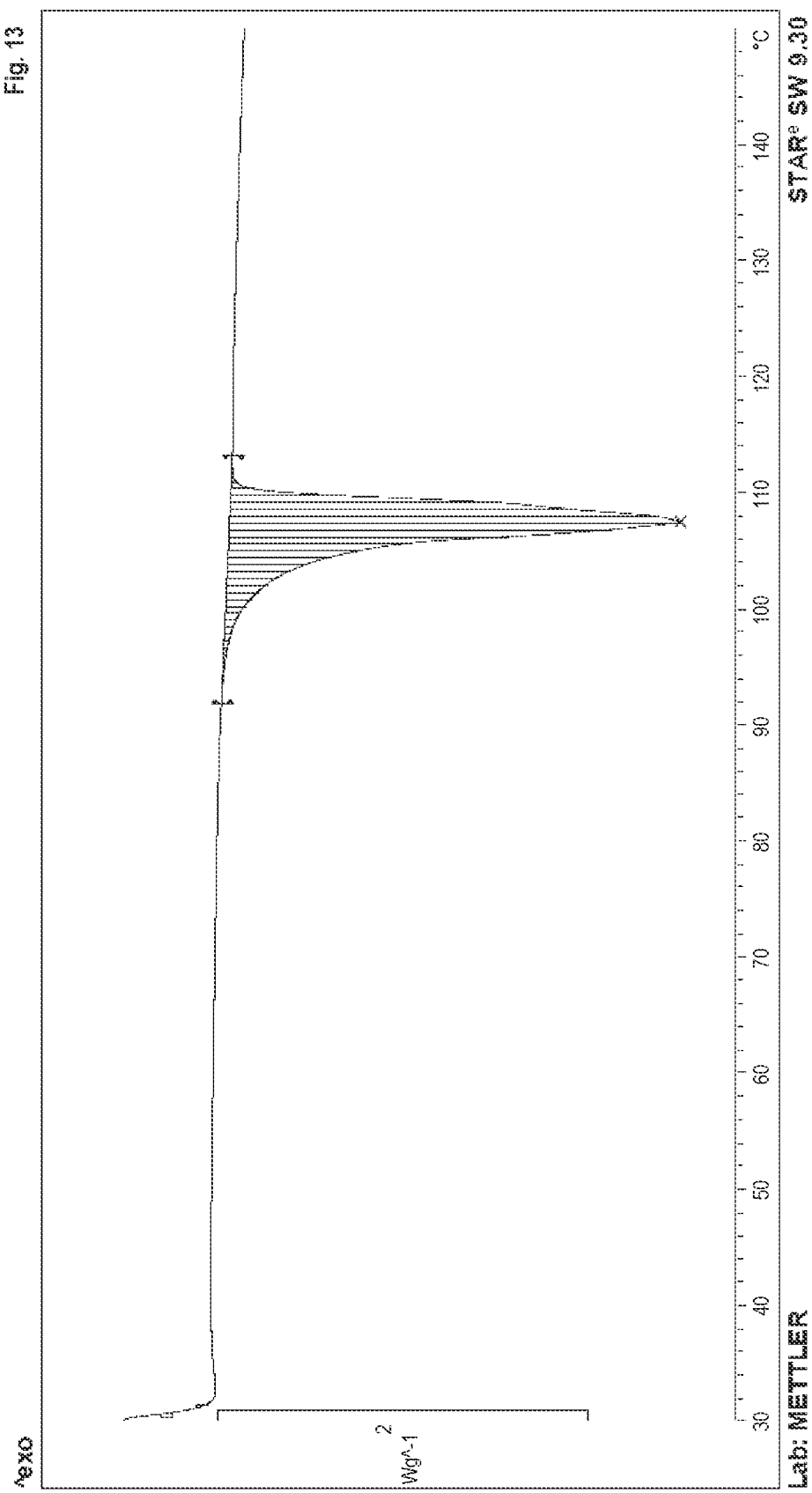

FIG. 13: DSC curve of treprostinil diethanolamine salt polymorph form B crystallized from MeOH/methyl tertiary-butyl ether mixture (peak: 107.42° C., example 12)

Figure 14:
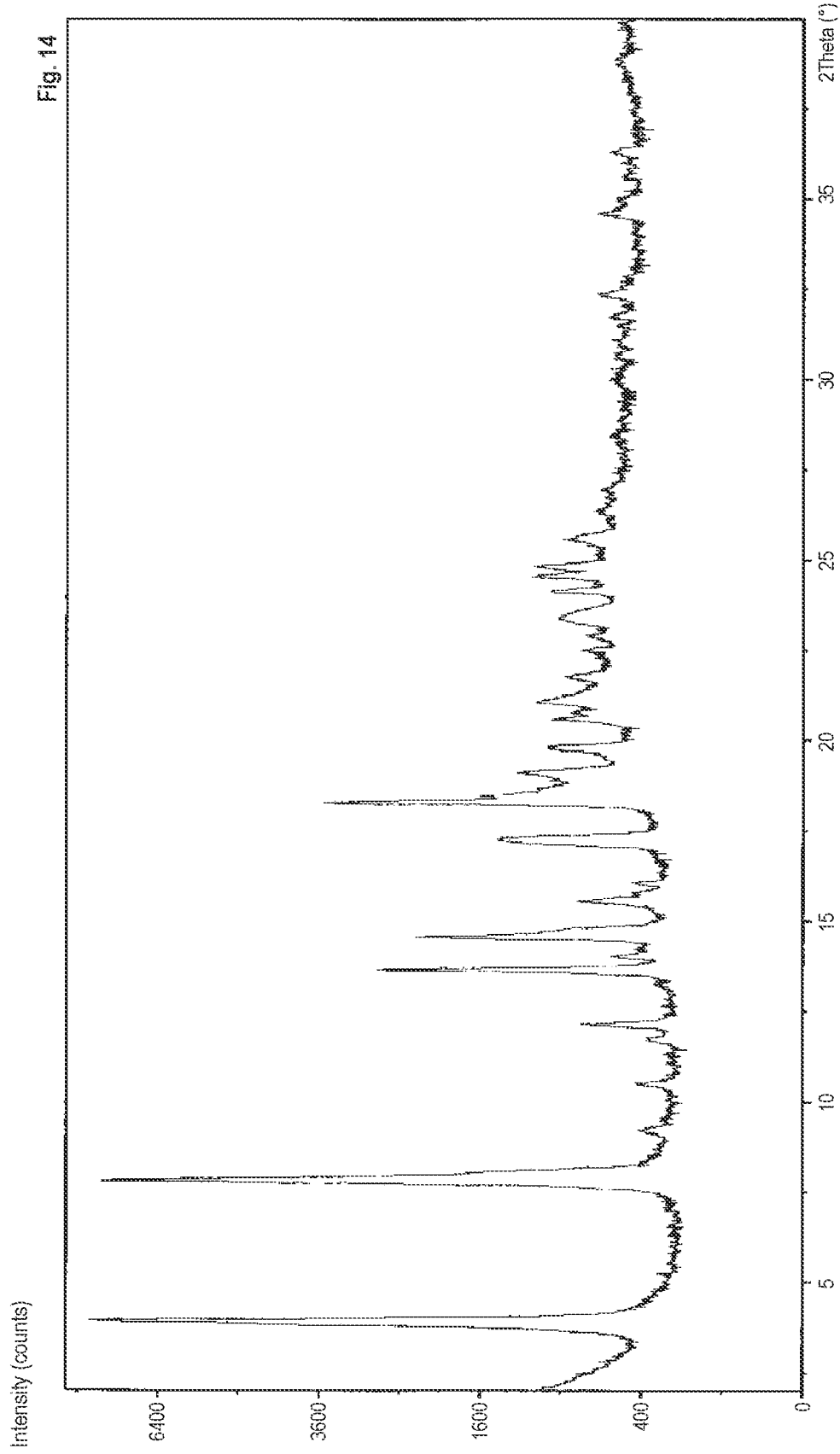

FIG. 14: XRPD pattern of treprostinil diethanolamine salt polymorph forms A+B crystallized from EtOH/ethyl acetate mixture (example 13)

Figure 15:
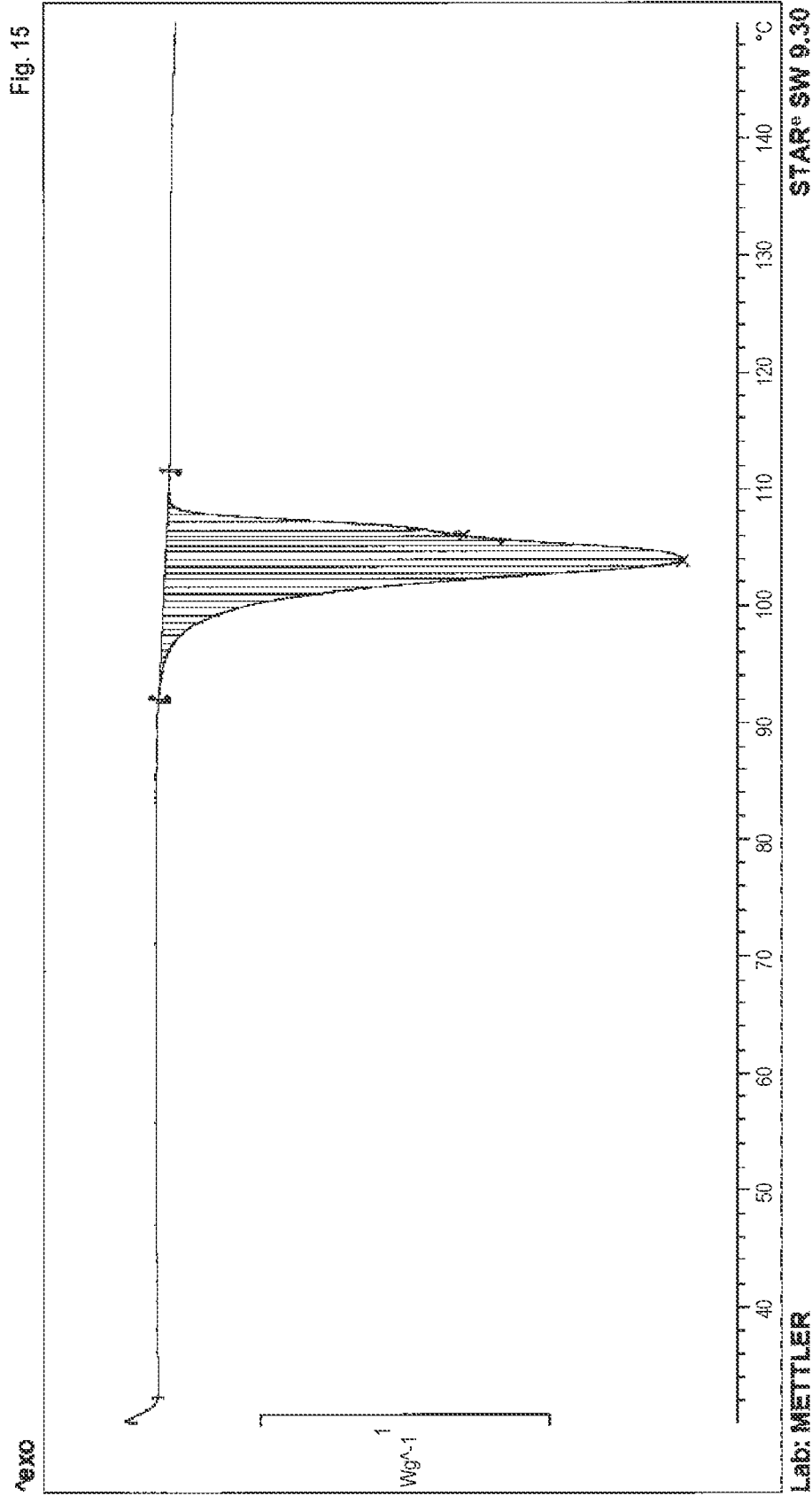

FIG. 15: DSC curve of treprostinil diethanolamine salt polymorph forms A+B crystallized from EtOH/ethyl acetate mixture (peaks: 103.84° C. and 105.94° C., example 13)

Figure 16:
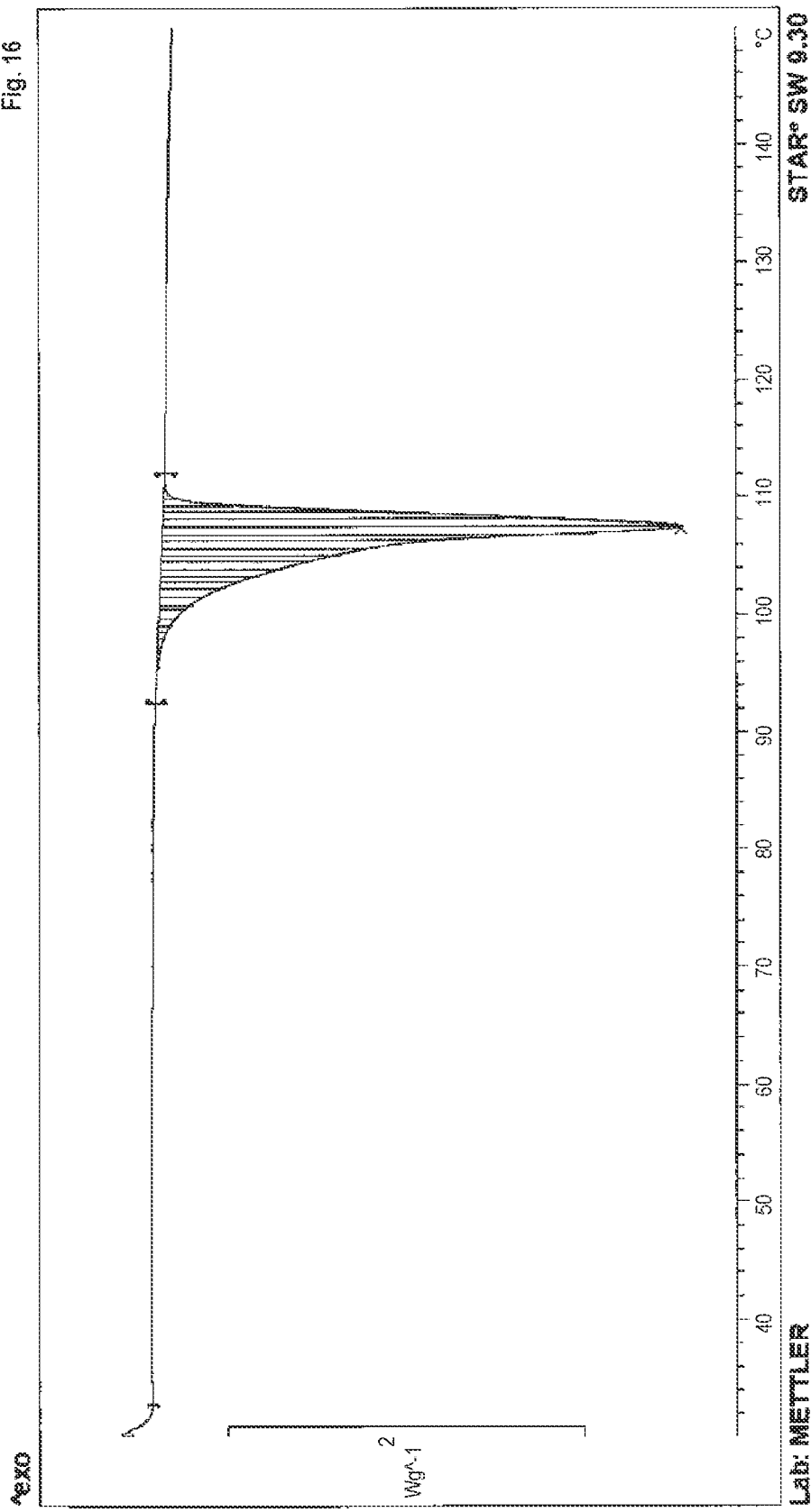

FIG. 16: DSC curve of treprostinil diethanolamine salt polymorph form B crystallized from MeOH/methyl tertiary-butyl ether mixture (peak: 107.34° C., example 14)

Figure 17:
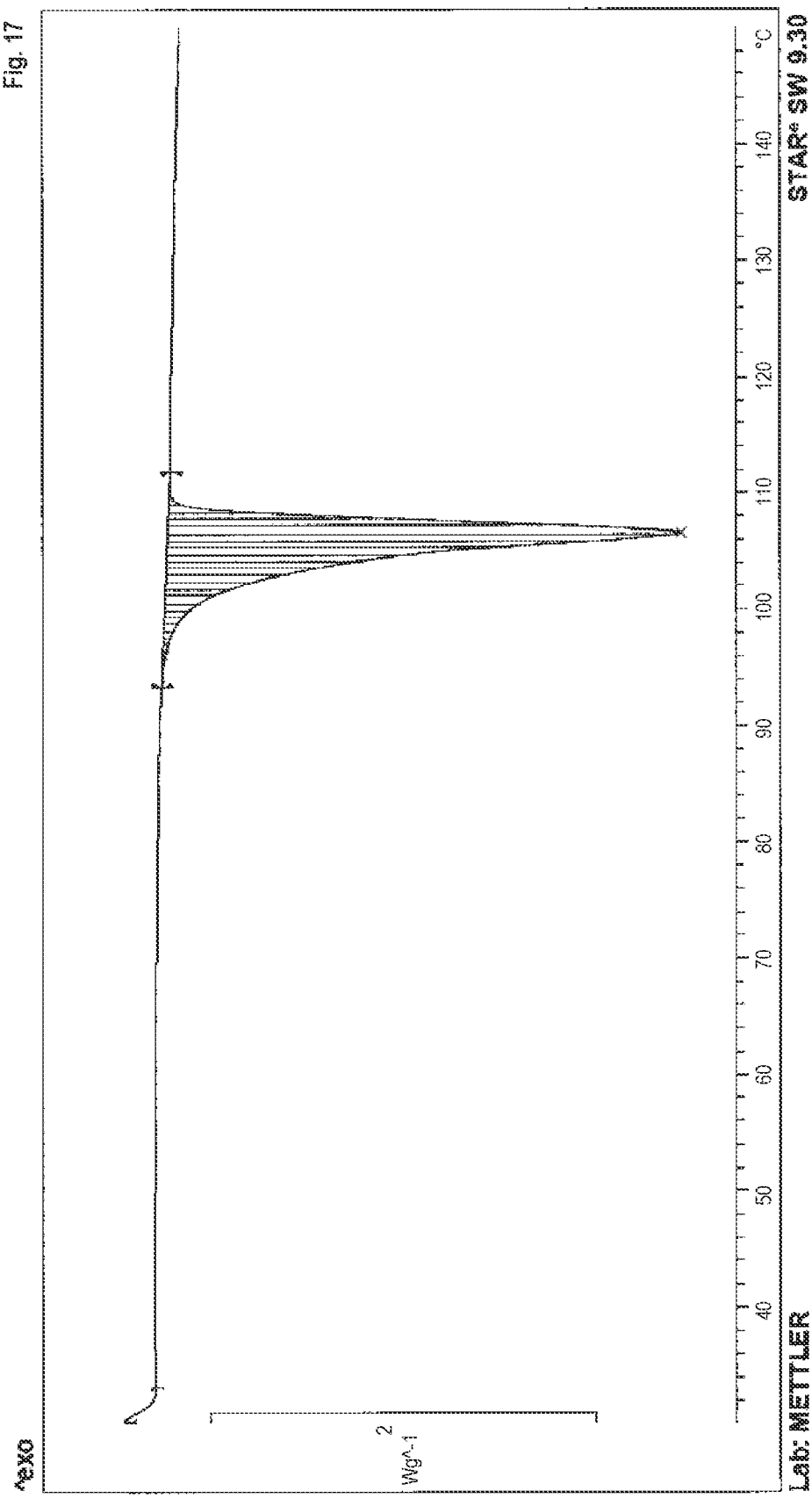

FIG. 17: DSC curve of treprostinil diethanolamine salt polymorph form B crystallized from MeOH/water/acetone mixture (peak: 106.56° C., example 15)

Figure 18:
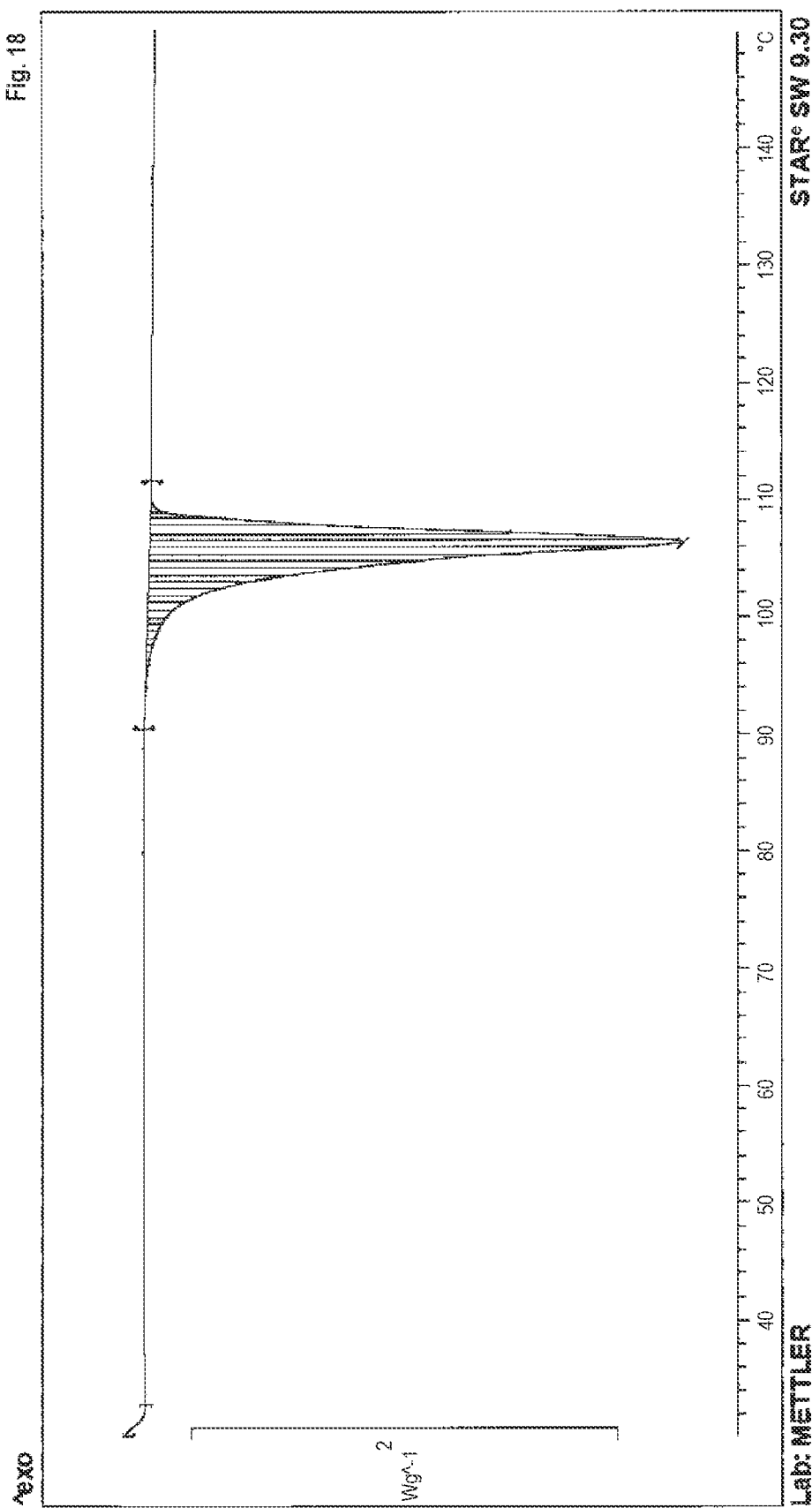

FIG. 18: DSC curve of treprostinil diethanolamine salt polymorph form B crystallized from MeOH/methyl tertiary-butyl ether mixture at 40° C. to 50° C. (peak: 106.23° C., example 16)

Figure 19:
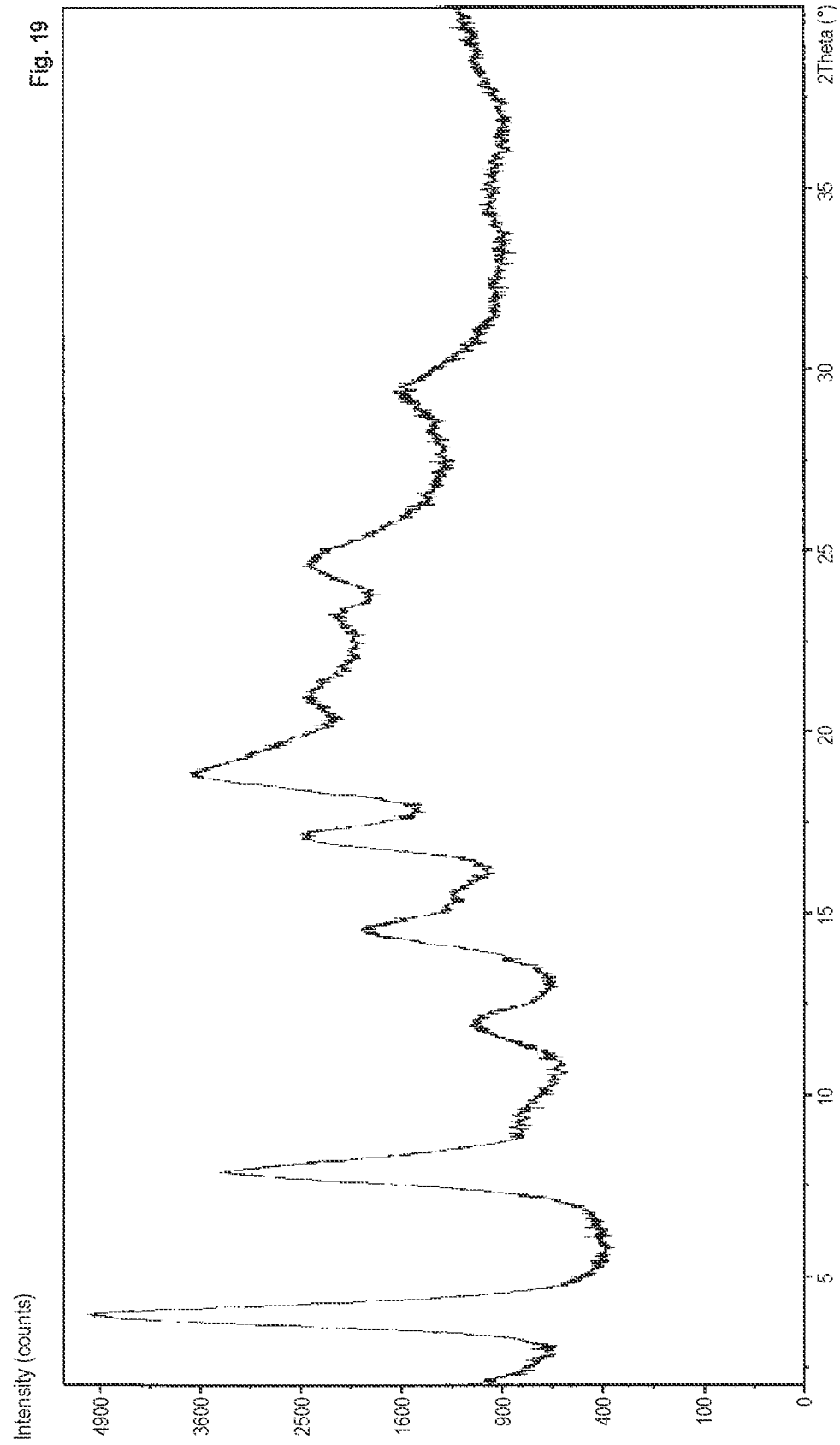

FIG. 19: XRPD pattern of treprostinil diethanolamine salt polymorph form C crystallized from MeOH/methyl tertiary-butyl ether mixture at −70° C. (example 17)

Figure 20:
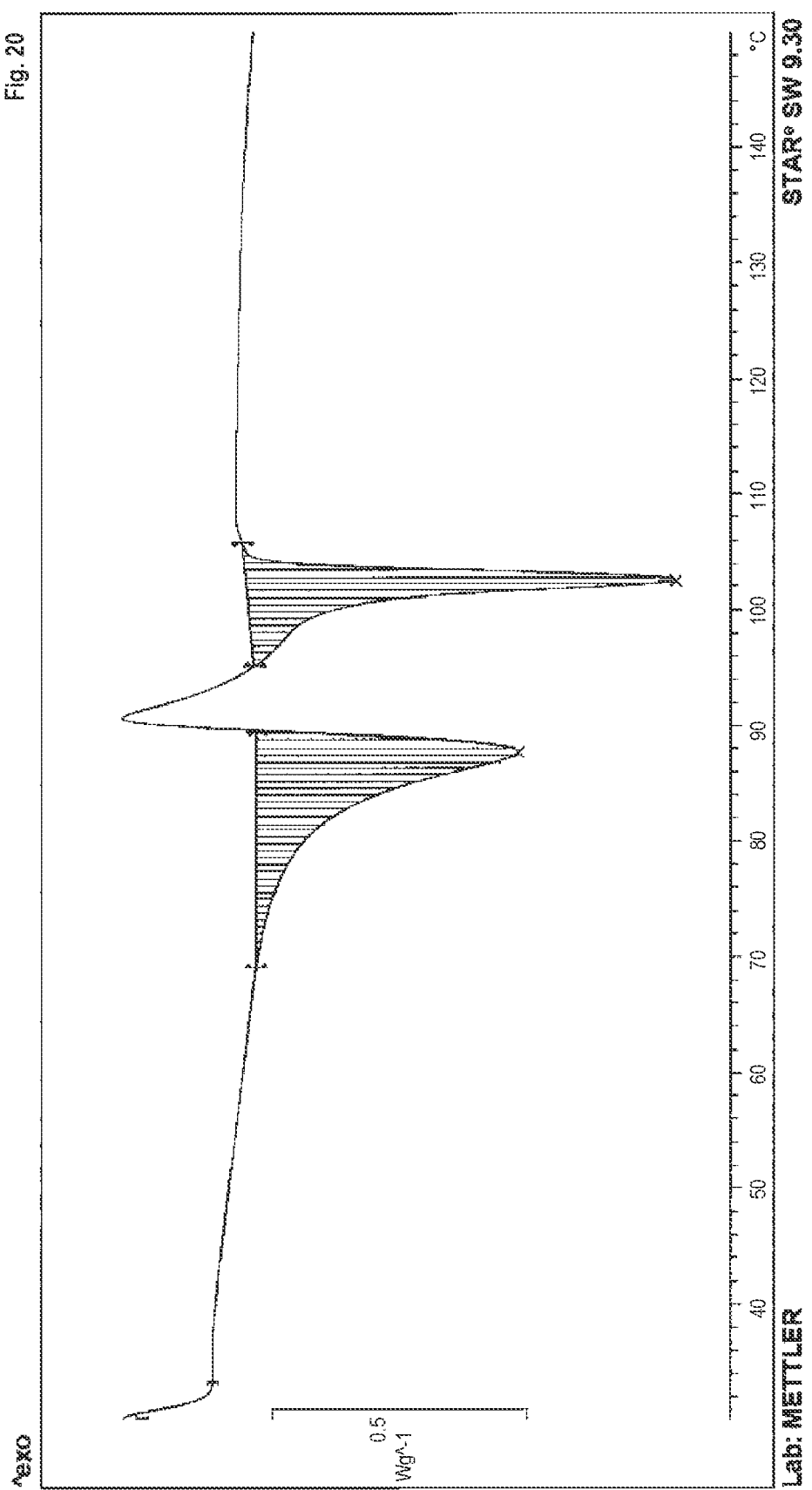

FIG. 20: DSC curve of treprostinil diethanolamine salt polymorph form C crystallized from MeOH/methyl tertiary-butyl ether mixture at −70° C. (peaks: 87.66° C. and 102.58° C., example 17)

FIG. 21: $^{13}C$ and $^{1}H$ NMR data of treprostinil diethanolamine salt acquired at 500 MHz in DMSO

EXAMPLES

Preparation of Treprostinil Diethanolamine Salt (I)

(1R,2R,3aS,9aS)-2-[2-Hydroxy-1-[3(S)-hydroxyoctyl]-2,3,3a,4,9,9a-hexahydro-1H-benz[f]inden-5-yloxy] acetic acid diethanolamine salt Example 1 (JIM-562/1)

1 g of treprostinil (II) is dissolved in 4 ml of methanol at room temperature. To the solution 0.3 g of diethanolamine (IV) is added and the reaction mixture is agitated at 35±5° C. for half an hour, then 15 ml of methyl tertiary-butyl ether (TBME) is added. The solution is filtered, seeded with approx. 10 mg of polymorph form B crystals, the suspension is agitated at room temperature for 2 hours and then 20 ml of methyl tertiary-butyl ether is added dropwise. Agitation is continued at room temperature for 16-24 hours, then the crystals are filtered off, washed and dried in vacuum at 45±5° C.

Yield: 1.15 g (91%), colorless crystals, corresponding to polymorph form B.

Example 2 (JIM-562/2)

1 g of treprostinil (II) is dissolved in 4 ml of methanol at room temperature. To the solution 0.3 g of diethanolamine (IV) is added and the reaction mixture is agitated at 35±5° C. for half an hour, then 15 ml of acetone is added, the solution is filtered, seeded with approx. 10 mg of polymorph form B crystals, agitated at room temperature for 2 hours, then 30 ml of acetone is added dropwise. The suspension is agitated at room temperature for 16-24 hours, then the crystals are filtered off, washed, and dried in vacuum at 45±5° C.

Yield: 0.92 g (73%), colorless crystals, corresponding to polymorph form B.

Example 3 (JIM-562/3)

1 g of treprostinil (II) is dissolved in 4 ml of methanol at room temperature. To the solution 0.3 g of diethanolamine (IV) is added and the reaction mixture is agitated at 35±5° C. for half an hour, then 15 ml of ethyl acetate is added, the solution is filtered, seeded with approx. 10 mg of polymorph form B crystals, agitated at room temperature for 2 hours, then 20 ml of ethyl acetate is added dropwise. The suspension is agitated at room temperature for 16-24 hours, then the crystals are filtered off, washed, and dried in vacuum at 45±5° C.

Yield: 1.16 g (92%), colorless crystals, corresponding to polymorph form B.

Example 4 (JIM-562/4)

1 g of treprostinil (II) is dissolved in 6 ml of methanol at room temperature. To the solution 0.3 g of diethanolamine (IV) is added, the reaction mixture is agitated at 35±5° C. for half an hour, then 10 ml of diisopropyl ether (DIPE) is added, the solution is filtered, seeded with approx. 10 mg of polymorph form B crystals, agitated at room temperature for 2 hours and then 20 ml of diisopropyl ether is added dropwise. The suspension is agitated at room temperature for 16-24 hours, then the crystals are filtered off, washed and dried in vacuum at 45±5° C.

Yield: 1.20 g (95%), colorless crystals, corresponding to polymorph form B.

Example 5 (JIM-562/5)

1 g of treprostinil (II) is dissolved in 6 ml of methanol at room temperature. To the solution 0.3 g of diethanolamine (IV) is added, the reaction mixture is agitated at 35±5° C. for half an hour, then 10 ml of toluene is added, the solution is filtered, seeded with approx. 10 mg of polymorph form B crystals, agitated at room temperature for 2 hours and then 30 ml of toluene is added dropwise. No crystallisation occurred.

Example 6 (JIM-562/6)

1 g of treprostinil (II) is dissolved in 4 ml of methanol at room temperature. To the solution 0.3 g of diethanolamine (IV) is added, the reaction mixture is agitated at 35±5° C. for half an hour, then 15 ml of acetonitrile is added, the solution is filtered, seeded with approx. 10 mg of polymorph form B crystals, agitated at room temperature for 2 hours an then 20 ml of acetonitrile is added dropwise. The suspension is agitated at room temperature for 16-24 hours, then the crystals are filtered off, washed, and dried in vacuum at 45±5° C. Yield: 1.15 g (91%), colorless crystals, corresponding to polymorph form B.

Powder X-ray diffractograms of the treprostinil diethanolamine salts prepared as described in examples 1-6 are demonstrated in FIG. 1

Example 7

70 g of treprostinil (II) is dissolved in 280 ml of methanol at 25±5° C. To the solution 20.73 g of diethanolamine (IV) is added and the reaction mixture is agitated at 35±5° C. for half an hour, then 1050 ml of methyl tertiary-butyl ether (TBME) is added. The solution is filtered into an apparatus equipped with stirrer, seeded with approx. 700 mg of polymorph form B crystals and agitated at room temperature for 2 hours, then 1400 ml of methyl tertiary-butyl ether is added dropwise. Agitation is continued at room temperature for 16-24 hours, then the crystals are filtered off, washed and dried in vacuum at 45±5° C.

Yield: 87.2 g (98%), colorless crystals, corresponding to polymorph form B.

Figure 2:
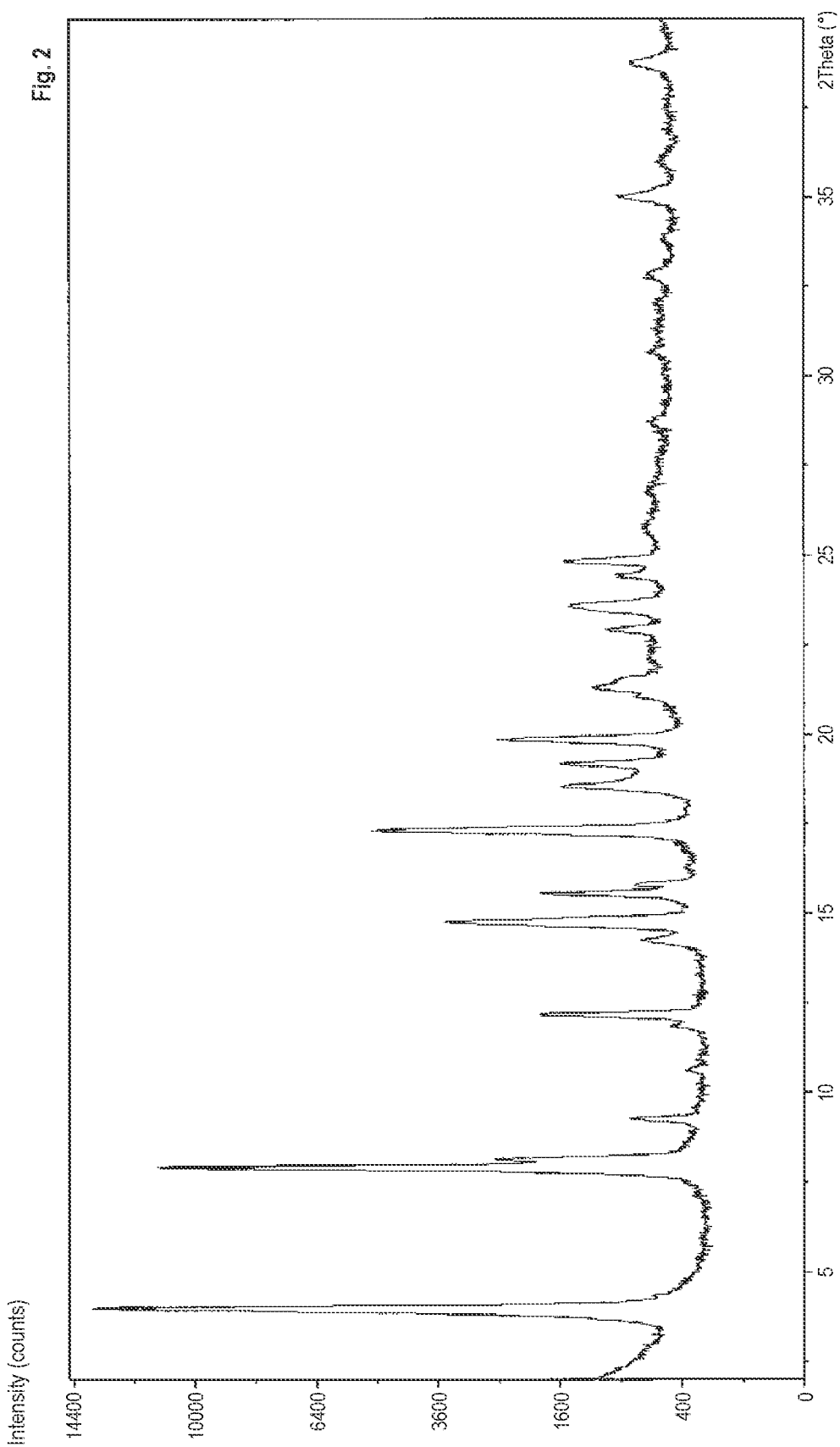
Figure 3:
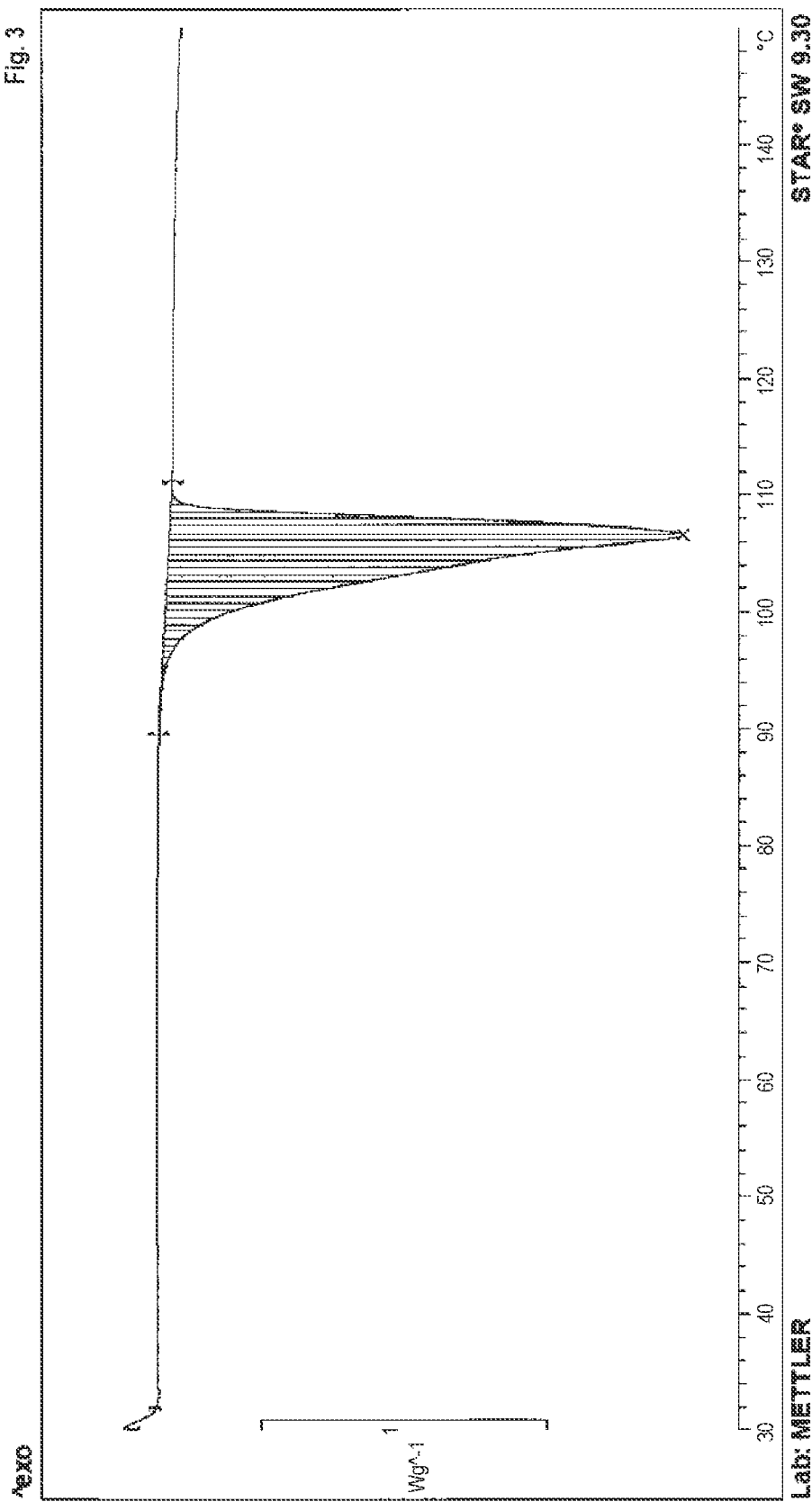

DSC curve is shown in FIG. 3, X-ray powder diffractogram in FIG. 2.

$^{13}$C and $^1$H NMR data of treprostinil diethylamine salt are demonstrated in FIG. 21.

Example 8

1 g of treprostinil (II) is dissolved in 4 ml of methanol at 25±5° C. To the solution 0.3 g of diethanolamine (IV) is added and the reaction mixture is agitated at 35±5° C. for half an hour, then 15 ml of methyl tertiary-butyl ether (TBME) is added. The solution is filtered into an apparatus fitted with stirrer, seeded with approx. 10 mg of polymorph form B crystals and agitated at room temperature for 2 hours, then 20 ml of methyl tertiary-butyl ether is added dropwise. Agitation is continued at room temperature for 16-24 hours, then the crystals are filtered off, washed and dried in vacuum at 45±5° C.

Yield: 1.15 g (91%), colorless crystals, corresponding to polymorph form B.

Figure 4:
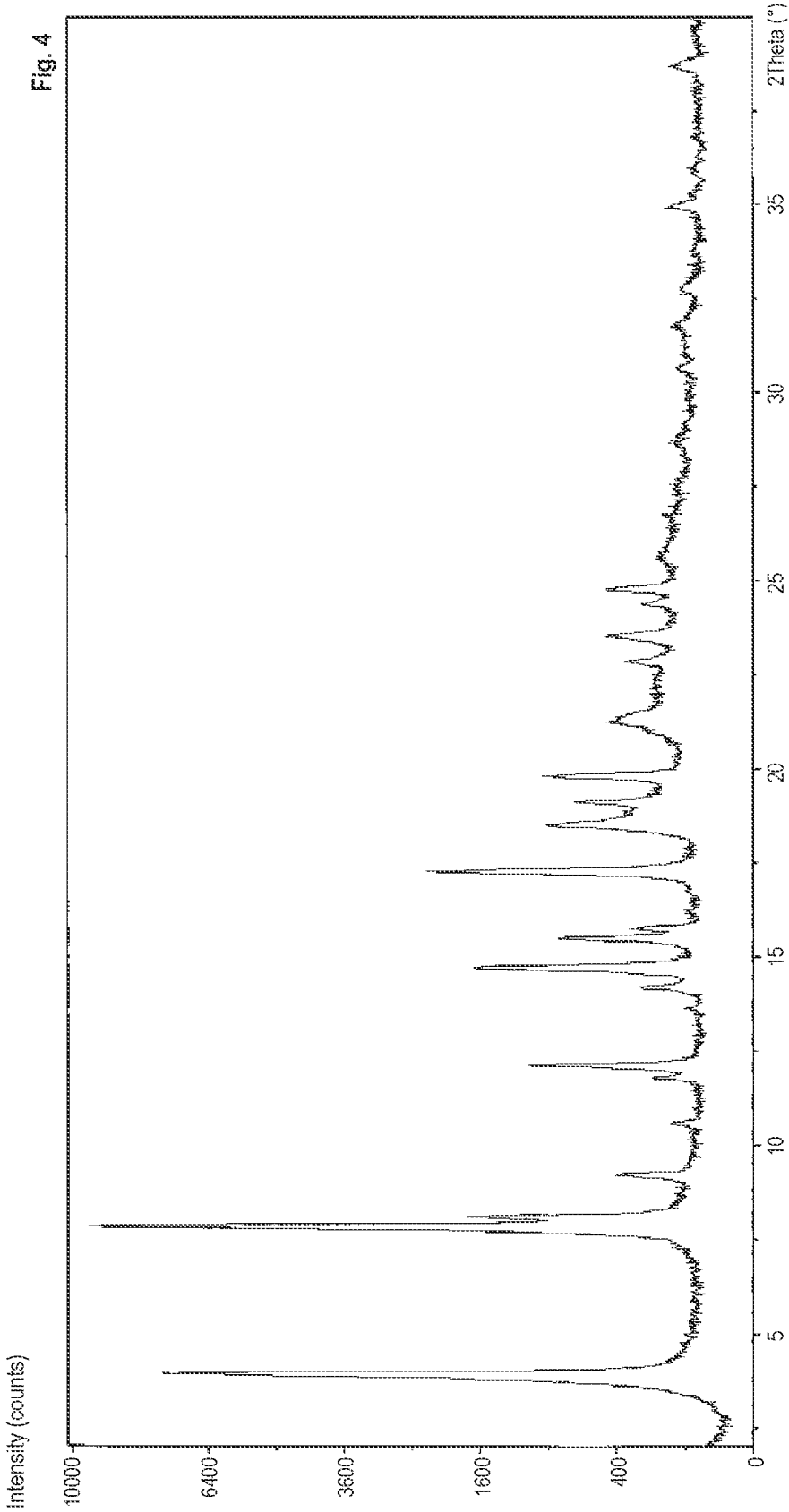
Figure 5:
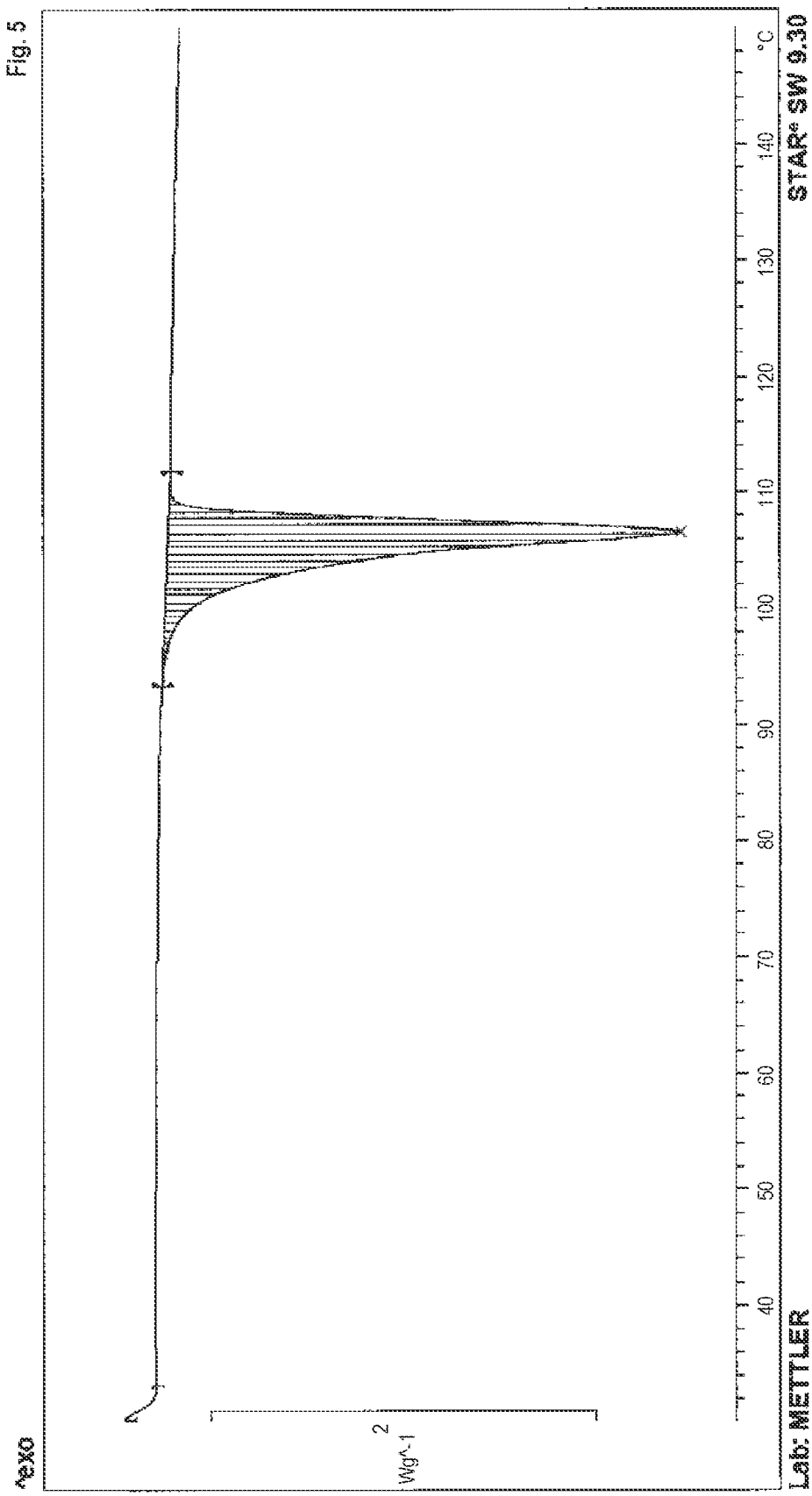

DSC curve is shown in FIG. 5, X-ray powder diffractogram in FIG. 4.

Example 9

1 g of treprostinil (II) is dissolved in 4 ml of methanol at 25±5° C. To the solution 0.3 g of diethanolamine (IV) is added and the reaction mixture is agitated at 35±5° C. for half an hour, then 15 ml of methyl tertiary-butyl ether (TBME) is added. The solution is filtered into an apparatus fitted with stirrer, seeded with approx. 10 mg of polymorph form B crystals and agitated at room temperature for 2 hours, then 25 ml of methyl tertiary-butyl ether is added dropwise. Agitation is continued at room temperature for 16-24 hours, then the crystals are filtered off, washed and dried in vacuum at 45±5° C.

Yield: 1.15 g (91%), colorless crystals, corresponding to polymorph form B.

Figure 6:
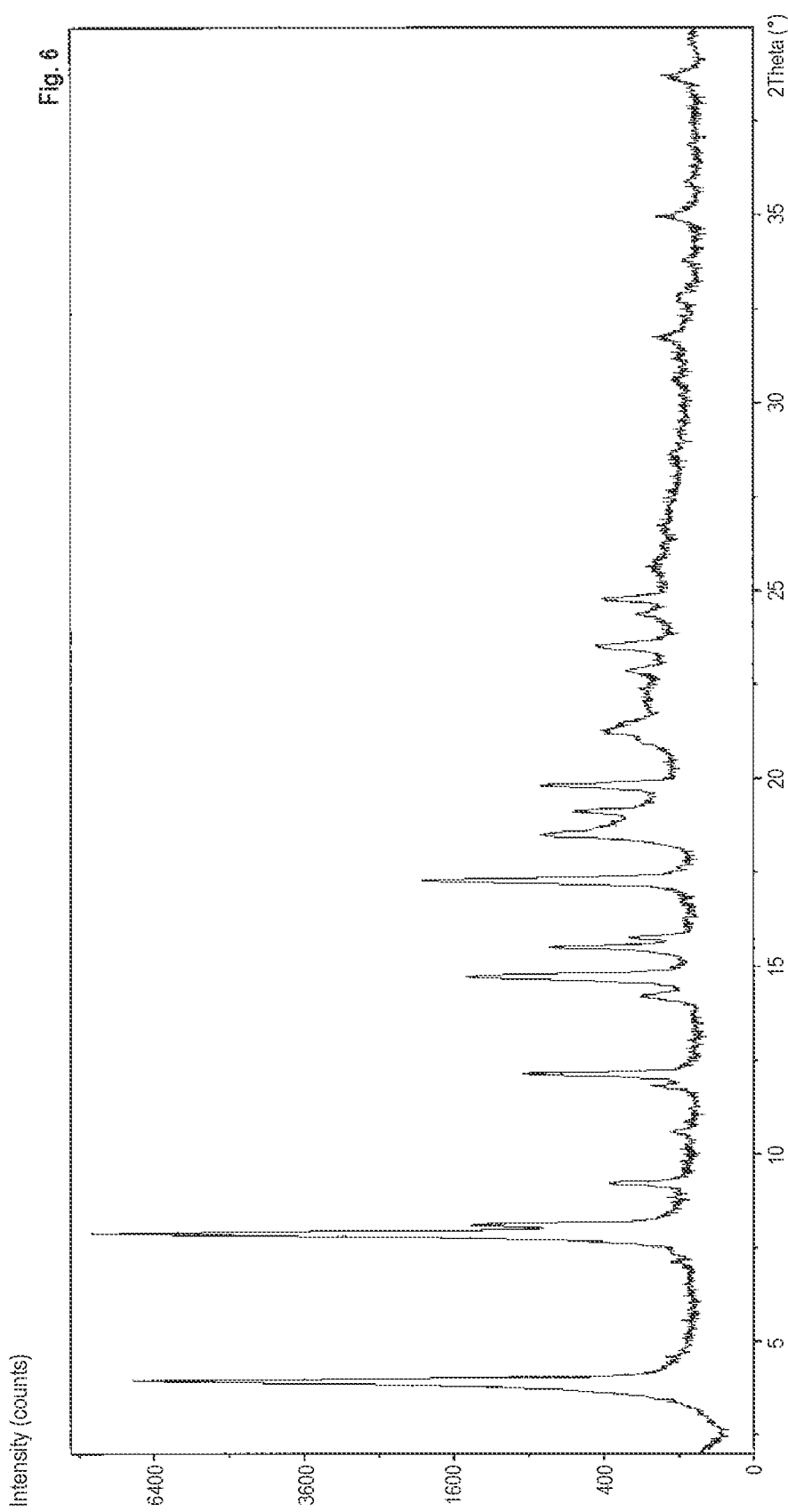
Figure 7:
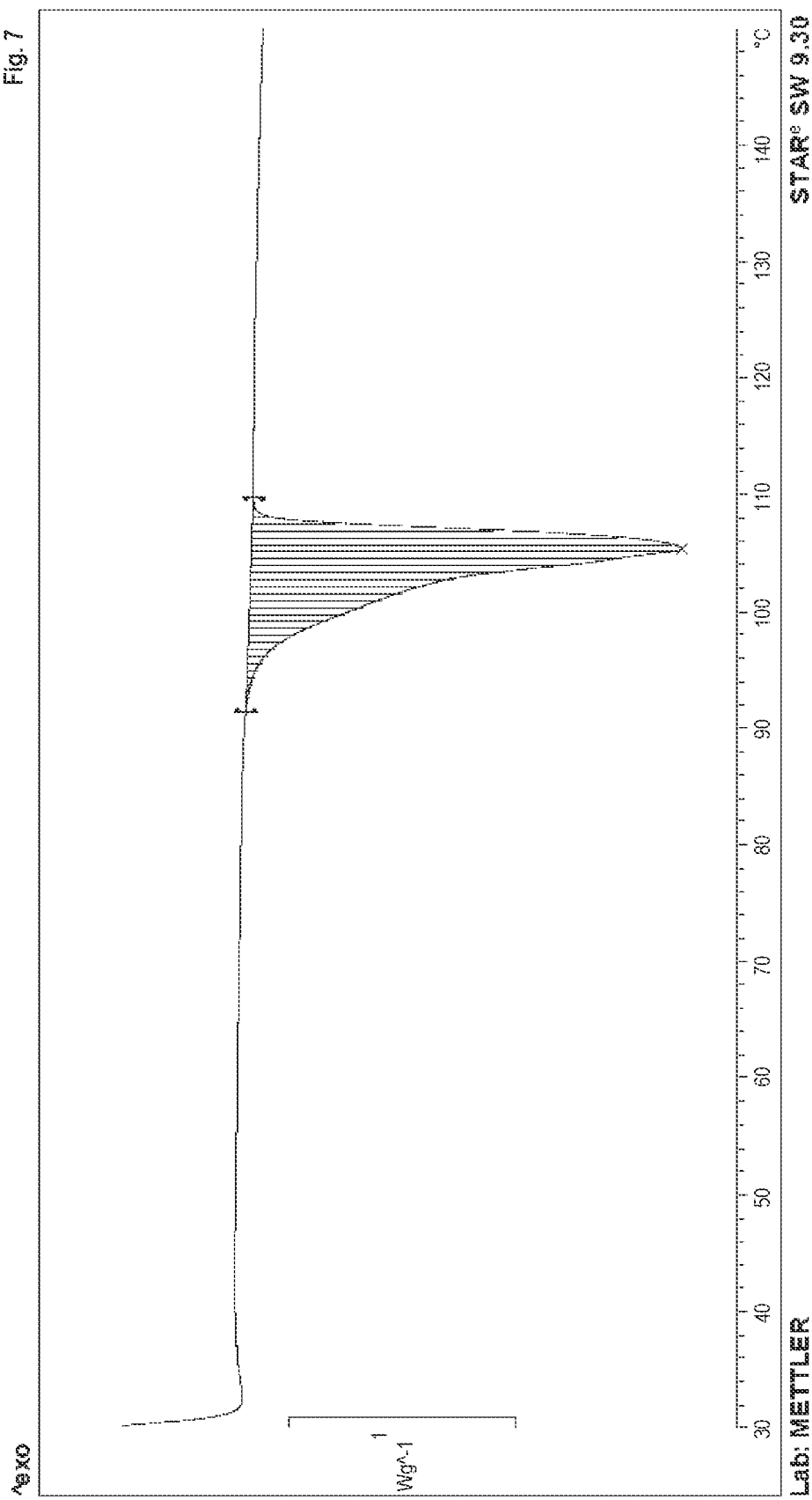

DSC curve is shown in FIG. 7, X-ray powder diffractogram in FIG. 6.

Example 10

1 g of treprostinil (II) is dissolved in 4 ml of methanol at 25±5° C. To the solution 0.3 g of diethanolamine (IV) is added and the reaction mixture is agitated at 35±5° C. for half an hour, then 15 ml of methyl tertiary-butyl ether (TBME) is added. The solution is filtered into an apparatus fitted with stirrer, seeded with approx. 10 mg of polymorph form B crystals and agitated at room temperature for 2 hours, then 29 ml of methyl tertiary-butyl ether is added dropwise. Agitation is continued at room temperature for 16-24 hours, then the crystals are filtered off, washed and dried in vacuum at 45±5° C.

Yield: 1.16 g (92%), colorless crystals, corresponding to polymorph form B.

Figure 8:
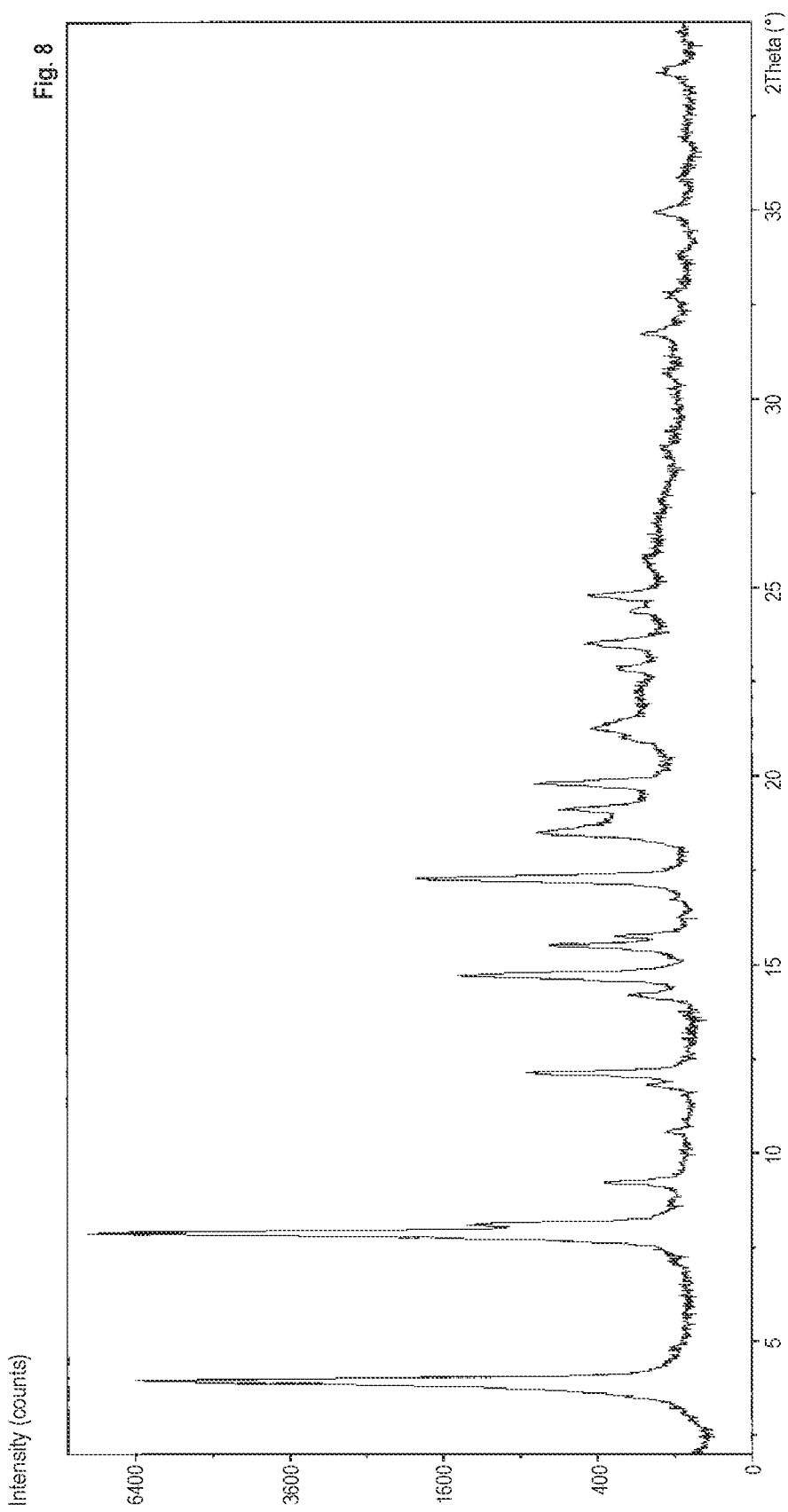

DSC curve is shown in FIG. 9, X-ray powder diffractogram in FIG. 8.

Example 11

1 g of treprostinil (II) is dissolved in 4 ml of methanol at 25±5° C. To the solution 0.3 g of diethanolamine (IV) is added and the reaction mixture is agitated at 35±5° C. for half an hour, then 15 ml of methyl tertiary-butyl ether (TBME) is added. The solution is filtered into an apparatus fitted with stirrer, seeded with approx. 10 mg of polymorph form B crystals and agitated at room temperature for 2 hours, then 9 ml of methyl tertiary-butyl ether is added dropwise. Agitation is continued at room temperature for 16-24 hours, then the crystals are filtered off, washed and dried in vacuum at 45±5° C.

Yield: 1.02 g (81%), colorless crystals, corresponding to polymorph form B.

DSC curve is shown in FIG. 11, X-ray powder diffractogram in FIG. 10.

Example 12

1 g of treprostinil (II) is dissolved in 4 ml of methanol at 25±5° C. To the solution 0.3 g of diethanolamine (IV) is added and the reaction mixture is agitated at 35±5° C. for half an hour, then 15 ml of methyl tertiary-butyl ether (TBME) is added. The solution is filtered into an apparatus fitted with stirrer, seeded with approx. 10 mg of polymorph form B crystals and agitated at room temperature for 2 hours, then 5 ml of methyl tertiary-butyl ether is added dropwise. Agitation is continued at room temperature for 16-24 hours, then the crystals are filtered off, washed and dried in vacuum at 45±5° C.

Yield: 0.95 g (75%), colorless crystals, corresponding to polymorph form B.

DSC curve is shown in FIG. 13, X-ray powder diffractogram in FIG. 12.

Example 13

1 g of treprostinil (II) is dissolved in 5 ml of ethanol at room temperature. To the solution 0.3 g of diethanolamine (IV) is added and the reaction mixture is agitated at 35±5° C. for half an hour, then 15 ml of ethyl acetate is added, the solution is filtered, seeded with approx. 10 mg of polymorph form B crystals, agitated at room temperature for 2 hours, then 20 ml of ethyl acetate (EtOH:EtOAc=1:7) is added dropwise. The suspension is agitated at room temperature for 16-24 hours, then the crystals are filtered off, washed and dried in vacuum at 45±5° C.

Yield: 1.1 g (87%), colourless crystals, mixture of polymorph forms A and B.

DSC curve is shown in FIG. 15, X-ray powder diffractogram in FIG. 14.

Example 14

1 g of treprostinil diethanolamine salt (I, mixture of polymorph forms A and B) is dissolved in 4 ml of methanol at 35±5° C. To the homogenous solution 15 ml of methyl tertiary-butyl ether is added at room temperature and the mixture is seeded with approx. 10 mg of polymorph form B crystals, agitated at room temperature for 2 hours, then 20 ml of methyl tertiary-butyl ether is added dropwise. Agitation is continued at room temperature for 16-24 hours, then the crystals are filtered off, washed and dried in vacuum at 45±5° C.

Yield: 1.23 g (97%), colorless crystals, corresponding to polymorph form B.

DSC curve is shown in FIG. 16.

Example 15

0.5 g of treprostinil diethanolamine salt is dissolved in a mixture of 2 ml of methanol and 0.6 ml of water at room temperature. To the homogenous solution 20 ml of acetone is dropped at room temperature, the opalescent solution is seeded with approx. 5 mg of polymorph form B crystals, agitated at room temperature for 2 hours, then 10 ml of acetone is added dropwise. After 20 hours of agitation the crystals are filtered off, washed and dried in vacuum at 45±5° C.

Yield: 0.39 g (61%), colorless crystals, corresponding to polymorph form B.

DSC curve is shown in FIG. 17.

Example 16

0.5 g of treprostinil diethanolamine salt is dissolved in 2 ml of methanol at 45±5° C. To the homogenous solution 20 ml of methyl tertiary-butyl ether is added at 45±5° C. and the mixture is seeded with approx. 5 mg of polymorph form B crystals. The opalescent solution is cooled to room temperature. After 20 hours of agitation the crystals are filtered off, washed and dried in vacuum at 45±5° C.

Yield: 0.55 g (87%), colorless crystals, corresponding to polymorph form B.

DSC curve is shown in FIG. 18.

Example 17

0.5 g of treprostinil diethanolamine salt is dissolved in 5 ml of methanol at −70° C. To the homogenous solution 30 ml of methyl tertiary-butyl ether is added at −70° C. and the mixture is seeded with approx. 5 mg of polymorph form B crystals. After 2 hours of agitation the opalescent solution is allowed to warm to room temperature. The not well filterable crystals are filtered off, washed and dried in vacuum at 45±5° C.

Yield: 0.31 g (49%), corresponding to polymorph form C.

DSC curve is shown in FIG. 20, X-ray powder diffractogram in FIG. 19.

The invention claimed is:

1. A process for the preparation of polymorph form B of treprostinil diethanolamine salt comprising the following steps:
   a. treprostinil is dissolved in methanol,
   b. to the solution of step a) diethanolamine or its solution in methanol is added,
   c. the reaction mixture of step b) is agitated till dissolution,
   d. after completion of salt formation in step c) a first portion of aprotic solvent is added to the solution,
   e. the solution of step d) is filtered,
   f. the filtrate of step e) is seeded with polymorph form B of treprostinil diethanolamine salt,
   g. to the crystal suspension obtained in step f), a second portion of the aprotic solvent is added,
   h. the suspension of step g) is agitated until crystallisation is completed,
   i. the crystals are separated, washed and dried;
   wherein ethers, ketone-type solvent, ester-type solvent, or acetonitrile are applied as aprotic solvent.

2. The process according to claim 1, wherein dissolution of treprostinil and diethanolamine is carried out at 25-50° C.

3. The process according to claim 2, wherein dissolution of treprostinil and diethanolamine is carried out at 30-40° C.

4. The process according to claim 1 wherein methyl tertiary-butyl ether is applied as aprotic solvent.

5. A process for the transformation of polymorph form A or the mixture of polymorph forms A and B of treprostinil diethanolamine salt into polymorph form B, comprising the following steps:
   a. treprostinil diethanolamine salt is dissolved in methanol,
   b. to the solution of step a) first portion of aprotic solvent is added,
   c. the solution of step b) is filtered,
   d. the filtrate of step c) is seeded with polymorph form B of treprostinil diethanolamine salt,
   e. to the crystal suspension obtained in step d), a second portion of the aprotic solvent is added,
   f. the suspension of step e) is agitated until crystallisation is completed,
   g. the crystals are separated, washed and dried;
   wherein ethers, polar ketone-type solvent, ester-type solvent, or acetonitrile are applied as aprotic solvent.

6. The process according to claim 5, wherein methyl tertiary-butyl ether is applied as aprotic solvent.

7. The process according to claim 5, wherein dissolution of treprostinil and diethanolamine is performed at 25-50° C.

8. The process according to claim 7, wherein dissolution of treprostinil and diethanolamine is performed at 30-40° C.

9. The process according to claim 6, wherein dissolution of treprostinil and diethanolamine is performed at 25-50° C.

10. The process according to claim 1, wherein methyl tertiary-butyl ether, diisopropyl ether, acetone, ethyl acetate, or acetonitrile is applied as aprotic solvent.

11. The process according to claim 5, wherein methyl tertiary-butyl ether, diisopropyl ether, acetone, ethyl acetate, or acetonitrile is applied as aprotic solvent.

12. The process according to claim 2, wherein methyl tertiary-butyl ether, diisopropyl ether, acetone, ethyl acetate, or acetonitrile is applied as aprotic solvent.

13. The process according to claim 3, wherein methyl tertiary-butyl ether, diisopropyl ether, acetone, ethyl acetate, or acetonitrile is applied as aprotic solvent.

14. The process according to claim 1, wherein the agitation in step h) is at room temperature.

15. The process according to claim 1, wherein a ratio of methanol to aprotic solvent is 1:5 to 1:10.

* * * * *